United States Patent
Hirai et al.

(10) Patent No.: US 11,732,313 B2
(45) Date of Patent: Aug. 22, 2023

(54) HIGH-SWEETENING-CONTENT STEVIA PLANT AND METHOD FOR SCREENING SAME

(71) Applicant: SUNTORY HOLDINGS LIMITED, Osaka (JP)

(72) Inventors: Tadayoshi Hirai, Kyoto (JP); Kazunari Iwaki, Kanagawa (JP); Katsuro Miyagawa, Kyoto (JP); Naoko Okitsu, Kyoto (JP); Saori Takeyama, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 56 days.

(21) Appl. No.: 17/259,309

(22) PCT Filed: Jul. 30, 2019

(86) PCT No.: PCT/JP2019/029896
§ 371 (c)(1),
(2) Date: Jan. 11, 2021

(87) PCT Pub. No.: WO2020/027155
PCT Pub. Date: Feb. 6, 2020

(65) Prior Publication Data
US 2021/0246517 A1 Aug. 12, 2021

(30) Foreign Application Priority Data
Jul. 31, 2018 (JP) .................. 2018-144512

(51) Int. Cl.
*C12Q 1/6895* (2018.01)
*A23L 27/30* (2016.01)
*A23L 2/60* (2006.01)

(52) U.S. Cl.
CPC .............. *C12Q 1/6895* (2013.01); *A23L 2/60* (2013.01); *A23L 27/36* (2016.08);
(Continued)

(58) Field of Classification Search
CPC .............. C12Q 1/6895; C12Q 2600/13; C12Q 2600/158; A23L 27/36; A23L 2/60; A23V 2002/00
See application file for complete search history.

(56) References Cited

U.S. PATENT DOCUMENTS

| | | |
|---|---|---|
| 2016/0021918 A1 | 1/2016 | Brower, III et al. |
| 2020/0170209 A1 | 6/2020 | Iwaki et al. |
| 2020/0281141 A1 | 9/2020 | Iwaki et al. |

FOREIGN PATENT DOCUMENTS

| | | |
|---|---|---|
| CN | 104472361 | 4/2015 |
| JP | 2009-517043 | 4/2009 |

(Continued)

OTHER PUBLICATIONS

Khan et al. "Physical and chemical mutagenesis in Stevia rebaudiana: variant generation with higher UGT expression and glycosidic profile but with low photosynthetic capabilities" (2016 Acta Physiol Plant 38:4, 12 total pages, DOI 10.1007/s11738-015-2003-8; of record IDS Apr. 13, 2021 (Year: 2016).*

(Continued)

*Primary Examiner* — Matthew R Keogh
*Assistant Examiner* — Rebecca Stephens
(74) *Attorney, Agent, or Firm* — Greenblum & Bernstein, P.L.C.

(57) ABSTRACT

The present invention provides a high sweet content *stevia* plant having a variation at a portion corresponding to SEQ ID NO: 1, a method of producing or screening for the same, etc.

17 Claims, 2 Drawing Sheets
Specification includes a Sequence Listing.

(52) U.S. Cl.
CPC ...... *A23V 2002/00* (2013.01); *C12Q 2600/13* (2013.01); *C12Q 2600/158* (2013.01)

(56) References Cited

FOREIGN PATENT DOCUMENTS

| | | | | |
|---|---|---|---|---|
| JP | 2016-515814 | 6/2016 | | |
| KR | 2014-0087559 | 7/2014 | | |
| WO | 2007/070224 | 6/2007 | | |
| WO | 2014/146084 | 9/2014 | | |
| WO | 2016/049531 | 3/2016 | | |
| WO | 2016/090460 | 6/2016 | | |
| WO | WO-2017098017 A1 * | 6/2017 | ............... | A23L 2/60 |
| WO | 2018/124142 | 7/2018 | | |
| WO | 2019/074089 | 4/2019 | | |

OTHER PUBLICATIONS

Gerami et al. "Effects of Ethyl Methanesulfonate on Morphological and Physiological Traits of Plants Regenerated From Stevia (Stevia Rebaudiana Bertoni) Calli" 2017 Applied Ecology and Environmental Research 15(3):373-385. (Year: 2017).*

Extended European Search Report issued in EP Patent Application No. 19843276.7, dated Mar. 29, 2022.

Khan et al., "Physical and Chemical Mutagenesis in *Stevia rebaudiana*: Variant Generation with Higher UGT Expression and Glycosidic Profile but with Low Photosynthetic Capabilities", *Acta Physiol. Plant.*, vol. 38, No. 4, 12 pages (2016).

International Search Report issued in PCT/JP2019/029896, dated Oct. 15, 2019, along with an English translation thereof.

* cited by examiner

[Figure 1]
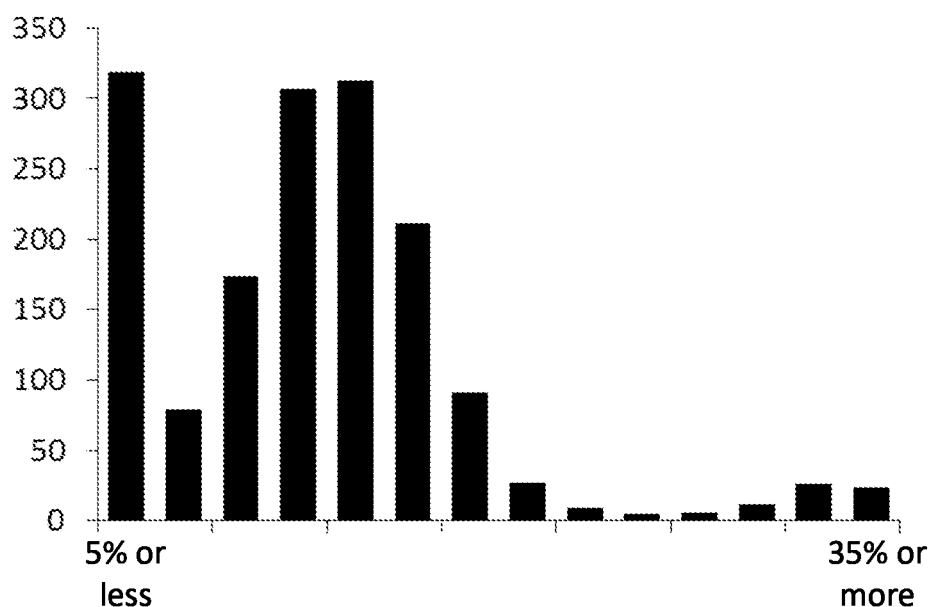
[Figure 2]
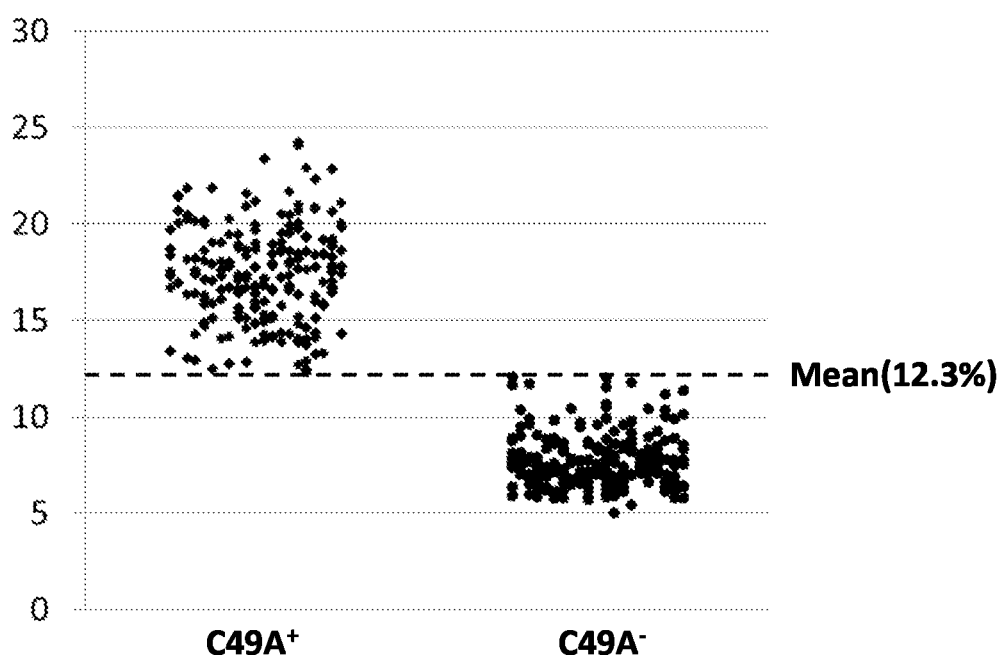

[Figure 3]
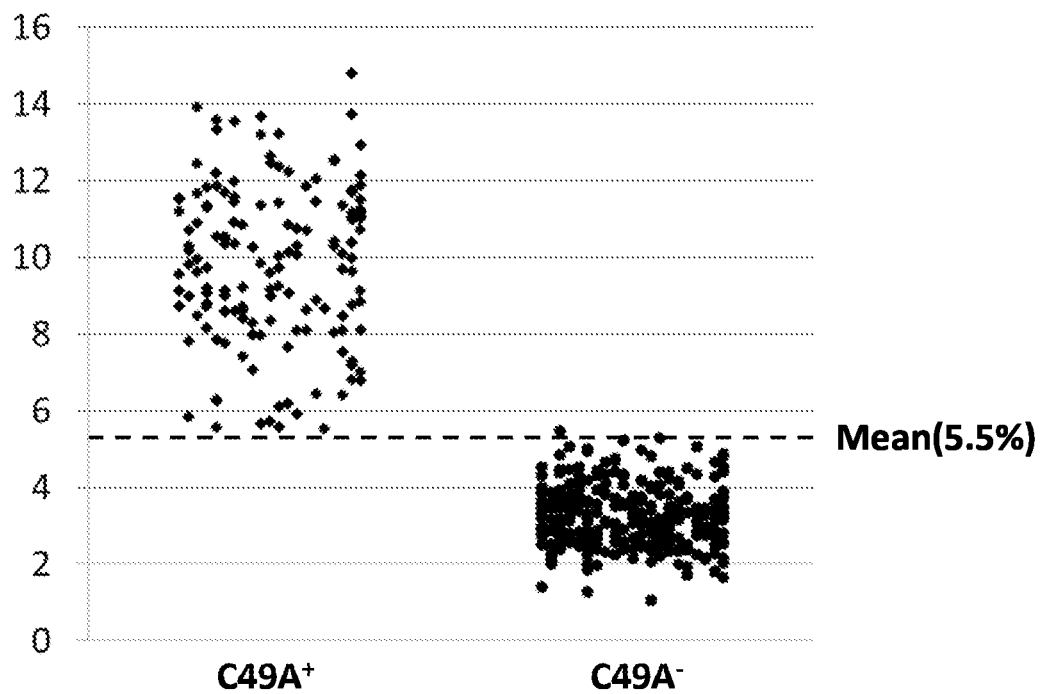

SEQUENCE LISTING

<160> NUMBER OF SEQ ID NOS: 102

<210> SEQ ID NO 1
<211> LENGTH: 367
<212> TYPE: DNA
<213> ORGANISM: Stevia rebaudiana

<400> SEQUENCE: 1

| ttatttaatg atccaatgga gggggtgatt caggtaataa aaggcattcg tatggaatat | 60 |
| accaaaacat tgcgattcgt tattagcatg gatctttcaa gtaataaact tatcggagaa | 120 |
| ataccagttg agttaactgc ccttcatgcc ttggtgagtc tcaatttgtc taataatcat | 180 |
| cttattggac acattccgaa tagcattgga aacatgaaag ctttaaattc tctagatttc | 240 |
| tcgagaaacg agttaaatgg gttgatccct ccaagcattg gagctttgaa ttttttgagt | 300 |
| catttaaatt tgtcaaacaa caacttatca ggaccaattc caatcggaaa tcaattgaga | 360 |
| accctca | 367 |

<210> SEQ ID NO 2
<211> LENGTH: 14
<212> TYPE: DNA
<213> ORGANISM: Stevia rebaudiana

<400> SEQUENCE: 2
ttatttaatg atcc    14

<210> SEQ ID NO 3
<211> LENGTH: 15
<212> TYPE: DNA
<213> ORGANISM: Stevia rebaudiana

<400> SEQUENCE: 3
ttatttaatg atcca    15

<210> SEQ ID NO 4
<211> LENGTH: 16
<212> TYPE: DNA
<213> ORGANISM: Stevia rebaudiana

<400> SEQUENCE: 4
ttatttaatg atccaa    16

<210> SEQ ID NO 5
<211> LENGTH: 17
<212> TYPE: DNA
<213> ORGANISM: Stevia rebaudiana

<400> SEQUENCE: 5
ttatttaatg atccaat    17

<210> SEQ ID NO 6
<211> LENGTH: 18
<212> TYPE: DNA
<213> ORGANISM: Stevia rebaudiana

<400> SEQUENCE: 6
ttatttaatg atccaatg    18

<210> SEQ ID NO 7
<211> LENGTH: 19
<212> TYPE: DNA
<213> ORGANISM: Stevia rebaudiana -continued

```
<400> SEQUENCE: 7
ttatttaatg atccaatgg                                               19

<210> SEQ ID NO 8
<211> LENGTH: 48
<212> TYPE: DNA
<213> ORGANISM: Stevia rebaudiana

<400> SEQUENCE: 8
ttatttaatg atccaatgga gggggtgatt caggtaataa aaggcatt               48

<210> SEQ ID NO 9
<211> LENGTH: 14
<212> TYPE: DNA
<213> ORGANISM: Stevia rebaudiana

<400> SEQUENCE: 9
tgagggttct caat                                                    14

<210> SEQ ID NO 10
<211> LENGTH: 15
<212> TYPE: DNA
<213> ORGANISM: Stevia rebaudiana

<400> SEQUENCE: 10
tgagggttct caatt                                                   15

<210> SEQ ID NO 11
<211> LENGTH: 16
<212> TYPE: DNA
<213> ORGANISM: Stevia rebaudiana

<400> SEQUENCE: 11
tgagggttct caattg                                                  16

<210> SEQ ID NO 12
<211> LENGTH: 17
<212> TYPE: DNA
<213> ORGANISM: Stevia rebaudiana

<400> SEQUENCE: 12
tgagggttct caattga                                                 17

<210> SEQ ID NO 13
<211> LENGTH: 18
<212> TYPE: DNA
<213> ORGANISM: Stevia rebaudiana

<400> SEQUENCE: 13
tgagggttct caattgat                                                18

<210> SEQ ID NO 14
<211> LENGTH: 19
<212> TYPE: DNA
<213> ORGANISM: Stevia rebaudiana

<400> SEQUENCE: 14
tgagggttct caattgatt                                               19

<210> SEQ ID NO 15
<211> LENGTH: 28
<212> TYPE: DNA
```

<210> SEQ ID NO 15
<211> LENGTH: 28
<212> TYPE: DNA
<213> ORGANISM: Stevia rebaudiana

<400> SEQUENCE: 15
tgagggttct caattgattt ccgattgg                                28

<210> SEQ ID NO 16
<211> LENGTH: 21
<212> TYPE: DNA
<213> ORGANISM: Stevia rebaudiana

<400> SEQUENCE: 16
aaaaggcatt cgtatggaat a                                       21

<210> SEQ ID NO 17
<211> LENGTH: 41
<212> TYPE: DNA
<213> ORGANISM: Stevia rebaudiana

<400> SEQUENCE: 17
ttcaggtaat aaaaggcatt cgtatggaat ataccaaaac a                 41

<210> SEQ ID NO 18
<211> LENGTH: 61
<212> TYPE: DNA
<213> ORGANISM: Stevia rebaudiana

<400> SEQUENCE: 18
gagggggtga ttcaggtaat aaaaggcatt cgtatggaat ataccaaaac attgcgattc    60
g                                                             61

<210> SEQ ID NO 19
<211> LENGTH: 81
<212> TYPE: DNA
<213> ORGANISM: Stevia rebaudiana

<400> SEQUENCE: 19
tgatccaatg gaggggtga ttcaggtaat aaaaggcatt cgtatggaat ataccaaaac     60
attgcgattc gttattagca t                                       81

<210> SEQ ID NO 20
<211> LENGTH: 367
<212> TYPE: DNA
<213> ORGANISM: Stevia rebaudiana

<400> SEQUENCE: 20
ttatttaatg atccaatgga ggggtgatt caggtaataa aaggcattag tatggaatat     60
accaaaacat tgcgattcgt tattagcatg gatctttcaa gtaataaact tatcggagaa   120
ataccagttg agttaactgc ccttcatgcc ttggtgagtc tcaatttgtc taataatcat   180
cttattggac acattccgaa tagcattgga aacatgaaag ctttaaattc tctagatttc   240
tcgagaaacg agtaaatgg gttgatccct ccaagcattg gagctttgaa ttttttgagt    300
catttaaatt tgtcaaacaa caacttatca ggaccaattc caatcggaaa tcaattgaga   360
accctca                                                       367

<210> SEQ ID NO 21
<211> LENGTH: 43
<212> TYPE: DNA
<213> ORGANISM: Artificial Sequence
<220> FEATURE:
<223> OTHER INFORMATION: Synthetic DNA

<400> SEQUENCE: 21
aaggttcttt atttttaaac ttatgttaat ttattgtatc tag                           43

<210> SEQ ID NO 22
<211> LENGTH: 21
<212> TYPE: DNA
<213> ORGANISM: Artificial Sequence
<220> FEATURE:
<223> OTHER INFORMATION: Synthetic DNA

<400> SEQUENCE: 22
ccttatgtac acatgctaca c                                                   21

<210> SEQ ID NO 23
<211> LENGTH: 383
<212> TYPE: DNA
<213> ORGANISM: Artificial Sequence
<220> FEATURE:
<223> OTHER INFORMATION: PCR product

<400> SEQUENCE: 23
aaggttcttt atttttaaac ttatgttaat ttattgtatc tagtagttaa tcaagagatg         60
ctctcttgga gaaattttat ggtcataaaa cctatatcaa agagatgctc tcttggtata        120
ttccatactt aaaatatcta ttttggaaaa aaagtgtagc atcttcctgc ttttagtagg        180
tgtcaatcat tattaaattt cacaaaaccg tgcaagaatc ccagtttccc tatagtttgt        240
atacgttcct gatctagtat tttacttatg tttcaaatca atccaatcat gcttgtgtcc        300
gaaaattaaa aaacaagggt attggatgcc ctgtaccact attattaact tttcagaaaa        360
acgtgtagca tgtgtacata agg                                                383

<210> SEQ ID NO 24
<211> LENGTH: 383
<212> TYPE: DNA
<213> ORGANISM: Artificial Sequence
<220> FEATURE:
<223> OTHER INFORMATION: PCR product

<400> SEQUENCE: 24
aaggttcttt atttttaaac ttatgttaat ttattgtatc tagaagttaa tcaagagatg         60
ctctcttgga gaaattttat ggtcataaaa cctatatcaa agagatgctc tcttggtata        120
ttccatactt aaaatatcta ttttggaaaa aaagtgtagc atcttcctgc ttttagtagg        180
tgtcaatcat tattaaattt cacaaaaccg tgcaagaatc ccagtttccc tatagtttgt        240
atacgttcct gatctagtat tttacttatg tttcaaatca gtccaatcat gcttgtgtcc        300
gaaaattaaa aaacaagggt attggatgcc ctgtaccact attattaact tttcagaaaa        360
acgtgtagca tgtgtacata agg                                                383

<210> SEQ ID NO 25
<211> LENGTH: 344
<212> TYPE: DNA
<213> ORGANISM: Artificial Sequence
<220> FEATURE:
<223> OTHER INFORMATION: Digested product

<400> SEQUENCE: 25
ctagaagtta atcaagagat gctctcttgg agaaatttta tggtcataaa acctatatca         60
aagagatgct ctcttggtat attccatact taaaatatct attttggaaa aaagtgtag         120

```
catcttcctg cttttagtag gtgtcaatca ttattaaatt tcacaaaacc gtgcaagaat    180
cccagtttcc ctatagtttg tatacgttcc tgatctagta ttttacttat gtttcaaatc    240
agtccaatca tgcttgtgtc cgaaaattaa aaaacaaggg tattggatgc cctgtaccac    300
tattattaac ttttcagaaa aacgtgtagc atgtgtacat aagg                     344

<210> SEQ ID NO 26
<211> LENGTH: 39
<212> TYPE: DNA
<213> ORGANISM: Artificial Sequence
<220> FEATURE:
<223> OTHER INFORMATION: Synthetic DNA

<400> SEQUENCE: 26
taatcatcca aaccctaatc tcgccaaaca accgggtac                            39

<210> SEQ ID NO 27
<211> LENGTH: 20
<212> TYPE: DNA
<213> ORGANISM: Artificial Sequence
<220> FEATURE:
<223> OTHER INFORMATION: Synthetic DNA

<400> SEQUENCE: 27
gaggaagaca ttggcaactc                                                 20

<210> SEQ ID NO 28
<211> LENGTH: 297
<212> TYPE: DNA
<213> ORGANISM: Artificial Sequence
<220> FEATURE:
<223> OTHER INFORMATION: PCR product

<400> SEQUENCE: 28
taatcatcca aaccctaatc tcgccaaaca accgggtact gatccaaacc ctgaaatgag     60
cacaactctt gaacctgatc acgagaatga agagcacaaa catgttatga cacatgtaaa    120
cgatggtttt tgctacatga aaaccctaga agacgaaacc cgtttaactg taaatcttga    180
aaacacattc tttgatgaaa aaccccttc gtatccggat cttatggact tttctgcatc     240
gaaaacggac gaatacgact tctatgatga acttgaagag ctgccaatgt cttcctc       297

<210> SEQ ID NO 29
<211> LENGTH: 297
<212> TYPE: DNA
<213> ORGANISM: Artificial Sequence
<220> FEATURE:
<223> OTHER INFORMATION: PCR product

<400> SEQUENCE: 29
taatcatcca aaccctaatc tcgccaaaca accgggtacc gatccaaacc ctgaaatgag     60
cacaactctt gaacctgatc acgagaatga agagcacaaa catgttatga cacatgtaaa    120
cgatggtttt tgctacatga aaaccctaga agacgaaacc cgtttaagtg taaatcttga    180
aaacacattc tttgatgaag aaccccttc gtatccggat cttatggact tttctgcatc     240
gaaaaaggac gaatacgact tctatgatga acttgaagag ttgccaatgt cttcctc       297

<210> SEQ ID NO 30
<211> LENGTH: 258
<212> TYPE: DNA
<213> ORGANISM: Artificial Sequence
<220> FEATURE:
<223> OTHER INFORMATION: Digested product
```

```
<400> SEQUENCE: 30
cgatccaaac cctgaaatga gcacaactct tgaacctgat cacgagaatg aagagcacaa      60
acatgttatg acacatgtaa acgatggttt tgctacatg aaaaccctag aagacgaaac      120
ccgtttaagt gtaaatcttg aaaacacatt ctttgatgaa gaaccccttt cgtatccgga      180
tcttatggac ttttctgcat cgaaaaagga cgaatacgac ttctatgatg aacttgaaga      240
gttgccaatg tcttcctc                                                   258

<210> SEQ ID NO 31
<211> LENGTH: 47
<212> TYPE: DNA
<213> ORGANISM: Artificial Sequence
<220> FEATURE:
<223> OTHER INFORMATION: Synthetic DNA

<400> SEQUENCE: 31
cgatggtttt tgctacatga aaaccctaga agacgaaacc cgcttaa                    47

<210> SEQ ID NO 32
<211> LENGTH: 23
<212> TYPE: DNA
<213> ORGANISM: Artificial Sequence
<220> FEATURE:
<223> OTHER INFORMATION: Synthetic DNA

<400> SEQUENCE: 32
accagcaata atccttgaat tag                                              23

<210> SEQ ID NO 33
<211> LENGTH: 390
<212> TYPE: DNA
<213> ORGANISM: Artificial Sequence
<220> FEATURE:
<223> OTHER INFORMATION: PCR product

<400> SEQUENCE: 33
cgatggtttt tgctacatga aaaccctaga agacgaaacc cgcttaactg taaatcttga      60
aaacacattc tttgatgaaa aaccccttc gtatccggat cttatggact tttctgcatc      120
gaaaacggac gaatacgact tctatgatga acttgaagag ctgccaatgt cttcctcatc     180
attcaaaagc ttcatgagaa gtaatttctt tgaggaaaga gttcttgttc aaccttattg     240
attaagaatt taagggaagc agattatata tgtaattaaa ttttggtatt tatactttga     300
acttaattaa taattataat aataatccca actagaggca cttagtggag attacttata     360
tataatacta attcaaggat tattgctggt                                      390

<210> SEQ ID NO 34
<211> LENGTH: 390
<212> TYPE: DNA
<213> ORGANISM: Artificial Sequence
<220> FEATURE:
<223> OTHER INFORMATION: PCR product

<400> SEQUENCE: 34
cgatggtttt tgctacatga aaaccctaga agacgaaacc cgcttaagtg taaatcttga      60
aaacacattc tttgatgaag aaccccttc gtatccggat cttatggact tttctgcatc      120
gaaaaaggac gaatacgact tctatgatga acttgaagag ttgccaatgt cttcctcatc     180
attcaaaagc ttcatgagaa gtaatttctt tgaggaaaga gttcttgttc aaccttattg     240
```

```
attaagaatt taagggaagc agattatata tgtaattaaa ttttggtatt tatactttga      300
acttaattaa taattataat aataatccca actagaggca cttagtggag attacttata      360
tataatacta attcaaggat tattgctggt                                       390
```

```
<210> SEQ ID NO 35
<211> LENGTH: 347
<212> TYPE: DNA
<213> ORGANISM: Artificial Sequence
<220> FEATURE:
<223> OTHER INFORMATION: Digested product

<400> SEQUENCE: 35
ttaagtgtaa atcttgaaaa cacattcttt gatgaagaac ccctttcgta tccggatctt      60
atggactttt ctgcatcgaa aaaggacgaa tacgacttct atgatgaact tgaagagttg     120
ccaatgtctt cctcatcatt caaaagcttc atgagaagta atttctttga ggaaagagtt     180
cttgttcaac cttattgatt aagaattaa gggaagcaga ttatatatgt aattaaattt      240
tggtatttat actttgaact taattaataa ttataataat aatcccaact agaggcactt     300
agtggagatt acttatatat aatactaatt caaggattat tgctggt                  347
```

```
<210> SEQ ID NO 36
<211> LENGTH: 20
<212> TYPE: DNA
<213> ORGANISM: Artificial Sequence
<220> FEATURE:
<223> OTHER INFORMATION: Synthetic DNA

<400> SEQUENCE: 36
cgcaaacacg tatactaatc                                                  20
```

```
<210> SEQ ID NO 37
<211> LENGTH: 20
<212> TYPE: DNA
<213> ORGANISM: Artificial Sequence
<220> FEATURE:
<223> OTHER INFORMATION: Synthetic DNA

<400> SEQUENCE: 37
tttagcatgg tatgtacaac                                                  20
```

```
<210> SEQ ID NO 38
<211> LENGTH: 140
<212> TYPE: DNA
<213> ORGANISM: Artificial Sequence
<220> FEATURE:
<223> OTHER INFORMATION: PCR product

<400> SEQUENCE: 38
cgcaaacacg tatactaatc acgtaacata tttttatttt ctaaattaaa atttgaatta      60
aagataacat aatatttatt tttagagtgt aacttctaaa aaatatcaac ctacgaaaaa     120
gttgtacata ccatgctaaa                                                 140
```

```
<210> SEQ ID NO 39
<211> LENGTH: 158
<212> TYPE: DNA
<213> ORGANISM: Artificial Sequence
<220> FEATURE:
<223> OTHER INFORMATION: PCR product

<400> SEQUENCE: 39
cgcaaacacg tatactaatc acgtaacata tttttatttt ctaaattaaa attttataac      60
```
aatatcatac ttgaattaaa gataacataa tatttatttt tagagtgtaa cttctaaaaa    120
atatcaacct acgaaaaagt tgtacatacc atgctaaa                            158

<210> SEQ ID NO 40
<211> LENGTH: 49
<212> TYPE: DNA
<213> ORGANISM: Artificial Sequence
<220> FEATURE:
<223> OTHER INFORMATION: Synthetic DNA

<400> SEQUENCE: 40
atacaaaaac acaacccata tggtcaaatc aacccattca tgagcgatc                 49

<210> SEQ ID NO 41
<211> LENGTH: 22
<212> TYPE: DNA
<213> ORGANISM: Artificial Sequence
<220> FEATURE:
<223> OTHER INFORMATION: Synthetic DNA

<400> SEQUENCE: 41
cccttgtaaa tcccatatgt ag                                              22

<210> SEQ ID NO 42
<211> LENGTH: 288
<212> TYPE: DNA
<213> ORGANISM: Artificial Sequence
<220> FEATURE:
<223> OTHER INFORMATION: PCR product

<400> SEQUENCE: 42
atacaaaaac acaacccata tggtcaaatc aacccattca tgagcgatca ggtcaaattc     60
gctatctgag ctgatgcatt caactatttg gtctcttttt aacatttatt ttttttatta   120
ttttgaatgt agaaactttg gaactactca actggtaagt tcttgaagat gtataccggt   180
catgtaaaca aaacatattg tataactccg acttttctg taacaaatgg aaaatatatt    240
gttagtggtt cagaagatca ttgtgtctac atatgggatt tacaaggg                288

<210> SEQ ID NO 43
<211> LENGTH: 288
<212> TYPE: DNA
<213> ORGANISM: Artificial Sequence
<220> FEATURE:
<223> OTHER INFORMATION: PCR product

<400> SEQUENCE: 43
atacaaaaac acaacccata tggtcaaatc aacccattca tgagcgatcg ggtcaaattc     60
gctatctgag ctgatgcatt caactatttg gtctcttttt aacatttatt ttttttatta   120
ttttgaatgt agaaactttg gaactactca actggtaagt tcttgaagat gtataccggt   180
catgtaaaca aaacatattg tataactccg acttttctg taacaaatgg aaaatatatt    240
gttagtggtt cagaagatca ttgtgtctac atatgggatt tacaaggg                288

<210> SEQ ID NO 44
<211> LENGTH: 240
<212> TYPE: DNA
<213> ORGANISM: Artificial Sequence
<220> FEATURE:
<223> OTHER INFORMATION: Digested product

<400> SEQUENCE: 44

```
cgggtcaaat tcgctatctg agctgatgca ttcaactatt tggtctctt ttaacattta      60 ttttttttat tatttgaat gtagaaactt tggaactact caactggtaa gttcttgaag     120
atgtataccg gtcatgtaaa caaaacatat tgtataactc cgacttttc tgtaacaaat    180 ggaaaatata tgttagtgg ttcagaagat cattgtgtct acatatggga tttacaaggg    240
```

<210> SEQ ID NO 45
<211> LENGTH: 60
<212> TYPE: DNA
<213> ORGANISM: Stevia rebaudiana

<400> SEQUENCE: 45

```
gagtaaaatc tataacgaca ctaaggtgga aaagaatat gtaagccaat tcgtagactt      60
```

<210> SEQ ID NO 46
<211> LENGTH: 60
<212> TYPE: DNA
<213> ORGANISM: Stevia rebaudiana

<400> SEQUENCE: 46

```
gagtaaaatc tataacgaca ctaaggtgga aaagaatat gtaagccaat tcgtagacta      60
```

<210> SEQ ID NO 47
<211> LENGTH: 20
<212> TYPE: DNA
<213> ORGANISM: Artificial Sequence
<220> FEATURE:
<223> OTHER INFORMATION: Synthetic DNA

<400> SEQUENCE: 47

```
ttcaggtaat aaaaggcctt                                                 20
```

<210> SEQ ID NO 48
<211> LENGTH: 20
<212> TYPE: DNA
<213> ORGANISM: Artificial Sequence
<220> FEATURE:
<223> OTHER INFORMATION: Synthetic DNA

<400> SEQUENCE: 48

```
ttcaggtaat aaaaggcact                                                 20
```

<210> SEQ ID NO 49
<211> LENGTH: 20
<212> TYPE: DNA
<213> ORGANISM: Artificial Sequence
<220> FEATURE:
<223> OTHER INFORMATION: Synthetic DNA

<400> SEQUENCE: 49

```
ttcaggtaat aaaaggctta                                                 20
```

<210> SEQ ID NO 50
<211> LENGTH: 20
<212> TYPE: DNA
<213> ORGANISM: Artificial Sequence
<220> FEATURE:
<223> OTHER INFORMATION: Synthetic DNA

<400> SEQUENCE: 50

```
ttcaggtaat aaaaggcttg                                                 20
```

<210> SEQ ID NO 51
<211> LENGTH: 20

```
<212> TYPE: DNA
<213> ORGANISM: Artificial Sequence
<220> FEATURE:
<223> OTHER INFORMATION: Synthetic DNA

<400> SEQUENCE: 51
ttcaggtaat aaaaggcctc                                                    20

<210> SEQ ID NO 52
<211> LENGTH: 20
<212> TYPE: DNA
<213> ORGANISM: Artificial Sequence
<220> FEATURE:
<223> OTHER INFORMATION: Synthetic DNA

<400> SEQUENCE: 52
ttcaggtaat aaaaggcacg                                                    20

<210> SEQ ID NO 53
<211> LENGTH: 20
<212> TYPE: DNA
<213> ORGANISM: Artificial Sequence
<220> FEATURE:
<223> OTHER INFORMATION: Synthetic DNA

<400> SEQUENCE: 53
ttcaggtaat aaaagtcatg                                                    20

<210> SEQ ID NO 54
<211> LENGTH: 20
<212> TYPE: DNA
<213> ORGANISM: Artificial Sequence
<220> FEATURE:
<223> OTHER INFORMATION: Synthetic DNA

<400> SEQUENCE: 54
ttcaggtaat aaaaggctrt                                                    20

<210> SEQ ID NO 55
<211> LENGTH: 20
<212> TYPE: DNA
<213> ORGANISM: Artificial Sequence
<220> FEATURE:
<223> OTHER INFORMATION: Synthetic DNA

<400> SEQUENCE: 55
ttcaggtaat aaaaggcttr                                                    20

<210> SEQ ID NO 56
<211> LENGTH: 20
<212> TYPE: DNA
<213> ORGANISM: Artificial Sequence
<220> FEATURE:
<223> OTHER INFORMATION: Synthetic DNA

<400> SEQUENCE: 56
ttcaggtaat aaaaggcagc                                                    20

<210> SEQ ID NO 57
<211> LENGTH: 20
<212> TYPE: DNA
<213> ORGANISM: Artificial Sequence
<220> FEATURE:
<223> OTHER INFORMATION: Synthetic DNA

<400> SEQUENCE: 57
```
ttcaggtaat aaaaggcycg                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic DNA

<400> SEQUENCE: 58
ttcaggtaat aaaagtgatc                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic DNA

<400> SEQUENCE: 59
ttcaggtaat aaaagggagg                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic DNA

<400> SEQUENCE: 60
ttcaggtaat aaaaggctgc                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic DNA

<400> SEQUENCE: 61
ttcaggtaat aaaaggaacc                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic DNA

<400> SEQUENCE: 62
ttcaggtaat aaaaggctga                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic DNA

<400> SEQUENCE: 63
ttcaggtaat aaaaggctgg                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic DNA

<400> SEQUENCE: 64
ttcaggtaat aaaagggtg                                    20

<210> SEQ ID NO 65
<211> LENGTH: 20
<212> TYPE: DNA
<213> ORGANISM: Artificial Sequence
<220> FEATURE:
<223> OTHER INFORMATION: Synthetic DNA

<400> SEQUENCE: 65
ttcaggtaat aaaaggtctg                                   20

<210> SEQ ID NO 66
<211> LENGTH: 20
<212> TYPE: DNA
<213> ORGANISM: Artificial Sequence
<220> FEATURE:
<223> OTHER INFORMATION: Synthetic DNA

<400> SEQUENCE: 66
ttcaggtaat aaaagggaag                                   20

<210> SEQ ID NO 67
<211> LENGTH: 20
<212> TYPE: DNA
<213> ORGANISM: Artificial Sequence
<220> FEATURE:
<223> OTHER INFORMATION: Synthetic DNA

<400> SEQUENCE: 67
ttcaggtaat aaaaggtcgt                                   20

<210> SEQ ID NO 68
<211> LENGTH: 20
<212> TYPE: DNA
<213> ORGANISM: Artificial Sequence
<220> FEATURE:
<223> OTHER INFORMATION: Synthetic DNA

<400> SEQUENCE: 68
ttcaggtaat aaaagttata                                   20

<210> SEQ ID NO 69
<211> LENGTH: 20
<212> TYPE: DNA
<213> ORGANISM: Artificial Sequence
<220> FEATURE:
<223> OTHER INFORMATION: Synthetic DNA

<400> SEQUENCE: 69
ttcaggtaat aaaaggctcg                                   20

<210> SEQ ID NO 70
<211> LENGTH: 20
<212> TYPE: DNA
<213> ORGANISM: Artificial Sequence
<220> FEATURE:
<223> OTHER INFORMATION: Synthetic DNA

<400> SEQUENCE: 70
ttcaggcgat aaaaggcgtt                                   20

<210> SEQ ID NO 71
<211> LENGTH: 20
<212> TYPE: DNA
<213> ORGANISM: Stevia rebaudiana

<400> SEQUENCE: 71
tgttttggta tattccatac                                                    20

<210> SEQ ID NO 72
<211> LENGTH: 48
<212> TYPE: DNA
<213> ORGANISM: Artificial Sequence
<220> FEATURE:
<223> OTHER INFORMATION: Synthetic DNA

<400> SEQUENCE: 72
ttatttaatg atccaatgga gggggtgatt caggtaataa aaggcctt                     48

<210> SEQ ID NO 73
<211> LENGTH: 48
<212> TYPE: DNA
<213> ORGANISM: Artificial Sequence
<220> FEATURE:
<223> OTHER INFORMATION: Synthetic DNA

<400> SEQUENCE: 73
ttatttaatg atccaatgga gggggtgatt caggtaataa aaggcact                     48

<210> SEQ ID NO 74
<211> LENGTH: 48
<212> TYPE: DNA
<213> ORGANISM: Artificial Sequence
<220> FEATURE:
<223> OTHER INFORMATION: Synthetic DNA

<400> SEQUENCE: 74
ttatttaatg atccaatgga gggggtgatt caggtaataa aaggctta                     48

<210> SEQ ID NO 75
<211> LENGTH: 48
<212> TYPE: DNA
<213> ORGANISM: Artificial Sequence
<220> FEATURE:
<223> OTHER INFORMATION: Synthetic DNA

<400> SEQUENCE: 75
ttatttaatg atccaatgga gggggtgatt caggtaataa aaggcttg                     48

<210> SEQ ID NO 76
<211> LENGTH: 48
<212> TYPE: DNA
<213> ORGANISM: Artificial Sequence
<220> FEATURE:
<223> OTHER INFORMATION: Synthetic DNA

<400> SEQUENCE: 76
ttatttaatg atccaatgga gggggtgatt caggtaataa aaggcctc                     48

<210> SEQ ID NO 77
<211> LENGTH: 48
<212> TYPE: DNA
<213> ORGANISM: Artificial Sequence
<220> FEATURE:
<223> OTHER INFORMATION: Synthetic DNA

<400> SEQUENCE: 77
ttatttaatg atccaatgga ggggtgatt caggtaataa aaggcacg        48

<210> SEQ ID NO 78
<211> LENGTH: 48
<212> TYPE: DNA
<213> ORGANISM: Artificial Sequence
<220> FEATURE:
<223> OTHER INFORMATION: Synthetic DNA

<400> SEQUENCE: 78
ttatttaatg atccaatgga ggggtgatt caggtaataa aagtcatg        48

<210> SEQ ID NO 79
<211> LENGTH: 48
<212> TYPE: DNA
<213> ORGANISM: Artificial Sequence
<220> FEATURE:
<223> OTHER INFORMATION: Synthetic DNA

<400> SEQUENCE: 79
ttatttaatg atccaatgga ggggtgatt caggtaataa aaggctrt        48

<210> SEQ ID NO 80
<211> LENGTH: 48
<212> TYPE: DNA
<213> ORGANISM: Artificial Sequence
<220> FEATURE:
<223> OTHER INFORMATION: Synthetic DNA

<400> SEQUENCE: 80
ttatttaatg atccaatgga ggggtgatt caggtaataa aaggcttr        48

<210> SEQ ID NO 81
<211> LENGTH: 48
<212> TYPE: DNA
<213> ORGANISM: Artificial Sequence
<220> FEATURE:
<223> OTHER INFORMATION: Synthetic DNA

<400> SEQUENCE: 81
ttatttaatg atccaatgga ggggtgatt caggtaataa aaggcagc        48

<210> SEQ ID NO 82
<211> LENGTH: 48
<212> TYPE: DNA
<213> ORGANISM: Artificial Sequence
<220> FEATURE:
<223> OTHER INFORMATION: Synthetic DNA

<400> SEQUENCE: 82
ttatttaatg atccaatgga ggggtgatt caggtaataa aaggcycg        48

<210> SEQ ID NO 83
<211> LENGTH: 48
<212> TYPE: DNA
<213> ORGANISM: Artificial Sequence
<220> FEATURE:
<223> OTHER INFORMATION: Synthetic DNA

<400> SEQUENCE: 83
ttatttaatg atccaatgga ggggtgatt caggtaataa aagtgatc        48

<210> SEQ ID NO 84
<211> LENGTH: 48
<212> TYPE: DNA

<213> ORGANISM: Artificial Sequence
<220> FEATURE:
<223> OTHER INFORMATION: Synthetic DNA

<400> SEQUENCE: 84
ttatttaatg atccaatgga gggggtgatt caggtaataa aagggagg                48

<210> SEQ ID NO 85
<211> LENGTH: 48
<212> TYPE: DNA
<213> ORGANISM: Artificial Sequence
<220> FEATURE:
<223> OTHER INFORMATION: Synthetic DNA

<400> SEQUENCE: 85
ttatttaatg atccaatgga gggggtgatt caggtaataa aaggctgc                48

<210> SEQ ID NO 86
<211> LENGTH: 48
<212> TYPE: DNA
<213> ORGANISM: Artificial Sequence
<220> FEATURE:
<223> OTHER INFORMATION: Synthetic DNA

<400> SEQUENCE: 86
ttatttaatg atccaatgga gggggtgatt caggtaataa aaggaacc                48

<210> SEQ ID NO 87
<211> LENGTH: 48
<212> TYPE: DNA
<213> ORGANISM: Artificial Sequence
<220> FEATURE:
<223> OTHER INFORMATION: Synthetic DNA

<400> SEQUENCE: 87
ttatttaatg atccaatgga gggggtgatt caggtaataa aaggctga                48

<210> SEQ ID NO 88
<211> LENGTH: 48
<212> TYPE: DNA
<213> ORGANISM: Artificial Sequence
<220> FEATURE:
<223> OTHER INFORMATION: Synthetic DNA

<400> SEQUENCE: 88
ttatttaatg atccaatgga gggggtgatt caggtaataa aaggctgg                48

<210> SEQ ID NO 89
<211> LENGTH: 48
<212> TYPE: DNA
<213> ORGANISM: Artificial Sequence
<220> FEATURE:
<223> OTHER INFORMATION: Synthetic DNA

<400> SEQUENCE: 89
ttatttaatg atccaatgga gggggtgatt caggtaataa aaggggtg                48

<210> SEQ ID NO 90
<211> LENGTH: 48
<212> TYPE: DNA
<213> ORGANISM: Artificial Sequence
<220> FEATURE:
<223> OTHER INFORMATION: Synthetic DNA

<400> SEQUENCE: 90
ttatttaatg atccaatgga gggggtgatt caggtaataa aaggtctg                48

<210> SEQ ID NO 91
<211> LENGTH: 48
<212> TYPE: DNA
<213> ORGANISM: Artificial Sequence
<220> FEATURE:
<223> OTHER INFORMATION: Synthetic DNA

<400> SEQUENCE: 91
ttatttaatg atccaatgga gggggtgatt caggtaataa aagggaag         48

<210> SEQ ID NO 92
<211> LENGTH: 48
<212> TYPE: DNA
<213> ORGANISM: Artificial Sequence
<220> FEATURE:
<223> OTHER INFORMATION: Synthetic DNA

<400> SEQUENCE: 92
ttatttaatg atccaatgga gggggtgatt caggtaataa aaggtcgt         48

<210> SEQ ID NO 93
<211> LENGTH: 48
<212> TYPE: DNA
<213> ORGANISM: Artificial Sequence
<220> FEATURE:
<223> OTHER INFORMATION: Synthetic DNA

<400> SEQUENCE: 93
ttatttaatg atccaatgga gggggtgatt caggtaataa aagttata         48

<210> SEQ ID NO 94
<211> LENGTH: 48
<212> TYPE: DNA
<213> ORGANISM: Artificial Sequence
<220> FEATURE:
<223> OTHER INFORMATION: Synthetic DNA

<400> SEQUENCE: 94
ttatttaatg atccaatgga gggggtgatt caggtaataa aaggctcg         48

<210> SEQ ID NO 95
<211> LENGTH: 48
<212> TYPE: DNA
<213> ORGANISM: Artificial Sequence
<220> FEATURE:
<223> OTHER INFORMATION: Synthetic DNA

<400> SEQUENCE: 95
ttatttaatg atccaatgga gggggtgatt caggcgataa aaggcgtt         48

<210> SEQ ID NO 96
<211> LENGTH: 367
<212> TYPE: DNA
<213> ORGANISM: Artificial Sequence
<220> FEATURE:
<223> OTHER INFORMATION: PCR product

<400> SEQUENCE: 96
ttatttaatg atccaatgga gggggtgatt caggtaataa aaggcactag tatggaatat    60
accaaaacat tgcgattcgt tattagcatg gatctttcaa gtaataaact tatcggagaa   120
ataccagttg agttaactgc ccttcatgcc ttggtgagtc tcaatttgtc taataatcat   180
cttattggac acattccgaa tagcattgga aacatgaaag ctttaaattc tctagatttc   240

```
tcgagaaacg agttaaatgg gttgatccct ccaagcattg gagctttgaa ttttttgagt    300
catttaaatt tgtcaaacaa caacttatca ggaccaattc caatcggaaa tcaattgaga    360
accctca                                                              367
```

<210> SEQ ID NO 97
<211> LENGTH: 367
<212> TYPE: DNA
<213> ORGANISM: Artificial Sequence
<220> FEATURE:
<223> OTHER INFORMATION: PCR product

<400> SEQUENCE: 97

```
ttatttaatg atccaatgga gggggtgatt caggtaataa aaggcactcg tatggaatat     60
accaaaacat tgcgattcgt tattagcatg gatctttcaa gtaataaact tatcggagaa    120
ataccagttg agttaactgc ccttcatgcc ttggtgagtc tcaatttgtc taataatcat    180
cttattggac acattccgaa tagcattgga aacatgaaag ctttaaattc tctagatttc    240
tcgagaaacg agttaaatgg gttgatccct ccaagcattg gagctttgaa ttttttgagt    300
catttaaatt tgtcaaacaa caacttatca ggaccaattc caatcggaaa tcaattgaga    360
accctca                                                              367
```

<210> SEQ ID NO 98
<211> LENGTH: 321
<212> TYPE: DNA
<213> ORGANISM: Artificial Sequence
<220> FEATURE:
<223> OTHER INFORMATION: Digested product

<400> SEQUENCE: 98

```
ctagtatgga ataccaaaa acattgcgat tcgttattag catggatctt tcaagtaata     60
aacttatcgg agaaatacca gttgagttaa ctgcccttca tgccttggtg agtctcaatt    120
tgtctaataa tcatcttatt ggacacattc cgaatagcat tggaaacatg aaagctttaa    180
attctctaga tttctcgaga aacgagttaa atgggttgat ccctccaagc attggagctt    240 tgaattttt gagtcattta aatttgtcaa acaacaactt atcaggacca attccaatcg    300
gaaatcaatt gagaaccctc a                                              321
```

<210> SEQ ID NO 99
<211> LENGTH: 21
<212> TYPE: DNA
<213> ORGANISM: Artificial Sequence
<220> FEATURE:
<223> OTHER INFORMATION: Synthetic DNA

<400> SEQUENCE: 99

```
aaaaggcatt agtatggaat a                                               21
```

<210> SEQ ID NO 100
<211> LENGTH: 41
<212> TYPE: DNA
<213> ORGANISM: Artificial Sequence
<220> FEATURE:
<223> OTHER INFORMATION: Synthetic DNA

<400> SEQUENCE: 100

```
ttcaggtaat aaaaggcatt agtatggaat ataccaaaac a                         41
```

<210> SEQ ID NO 101
<211> LENGTH: 61

```
<212> TYPE: DNA
<213> ORGANISM: Artificial Sequence
<220> FEATURE:
<223> OTHER INFORMATION: Synthetic DNA

<400> SEQUENCE: 101 gaggggtga ttcaggtaat aaaaggcatt agtatggaat ataccaaaac attgcgattc    60
g                                                                   61

<210> SEQ ID NO 102
<211> LENGTH: 81
<212> TYPE: DNA
<213> ORGANISM: Artificial Sequence
<220> FEATURE:
<223> OTHER INFORMATION: Synthetic DNA

<400> SEQUENCE: 102
tgatccaatg gaggggtga ttcaggtaat aaaaggcatt agtatggaat ataccaaaac    60
attgcgattc gttattagca t                                             81
```

HIGH-SWEETENING-CONTENT STEVIA PLANT AND METHOD FOR SCREENING SAME

TECHNICAL FIELD

The present invention relates to a *stevia* plant with high sweet content and method of screening for same.

BACKGROUND ART

In response to consumers' diversified needs, various drinks have been developed and are commercially available. Saccharides such as sucrose are components very commonly blended in drinks for the purpose of, for example, conferring sweetness. However, their influence on health due to excessive consumption has been pointed out. Thus, there are growing needs for lower calorie and naturally derived sweeteners. For example, Patent Literature 1 discloses a functional sweetener composition containing a vitamin, a high intensity sweetener, and a sweetness improving composition.

Rebaudioside (hereinafter, also referred to as "Reb") is known as a sweet component contained in a *stevia* extract. The *stevia* extract is obtained by extraction and purification from *stevia* dried leaves. *Stevia* is a perennial plant of the family Compositae with Paraguay in the South America as its place of origin, and its scientific name is *Stevia rebaudiana* Bertoni. *Stevia* contains a component having approximately 300 or more times the sweetness of sugar and is therefore cultivated for use of this sweet component extracted therefrom as a natural sweetener. The presence of various glycosides such as RebA, RebB, RebC, RebD, RebE and RebM has been reported as Reb (JP 2012-504552 A). Among various Rebs, for example, RebA is evaluated as a high intensity sweetener having good quality of sweetness and is widely used. The other Rebs have also been increasingly found to have their unique sweetness and associated taste.

Under these circumstances, a *stevia* plant reportedly having high content of specific rebaudioside is known (Patent Literatures 2 to 4).

CITATION LIST

Patent Literature

Patent Literature 1: JP 2009-517043 A
Patent Literature 2: National Publication of International Patent Application No. 2016-515814 A
Patent Literature 3: International Publication No. WO 2016/090460
Patent Literature 4: International Publication No. WO 2018/124142

DISCLOSURE OF THE INVENTION

Problems to be Solved by the Invention

There is an increasing need for a sweet component contained in a *stevia* plant.

Means for Solving the Problems

In one aspect, the present invention provides the following.

[1] A method of screening for a high sweet content *stevia* plant, comprising a step of detecting a variation at a portion corresponding to SEQ ID NO: 1 from the genome of a test *stevia* plant.
[2] The method according to [1], wherein the portion corresponding to SEQ ID NO: 1 is a portion of the genome of a test *stevia* plant which is amplified by PCR using a forward primer selected from SEQ ID NOs: 2 to 8 and a reverse primer selected from SEQ ID NOs: 9 to 15.
[3] The method according to [1] or [2], wherein the variation comprises a variation from C to A at a position corresponding to position 49 of SEQ ID NO: 1.
[4] The method according to any one of [1] to [3], wherein the step of detecting a variation is performed by use of dCAPS method or TaqMan PCR method.
[5] The method according to any one of [1] to [4], further comprising a step of determining the content of the sweet component of a test *stevia* plant tissue for which the variation has been detected.
[6] The method according to any one of [1] to [5], wherein the test *stevia* plant belongs to a segregating population obtained from crossing parents, at least one of which heterozygously has the variation at the portion corresponding to SEQ ID NO: 1, and the content of the sweet component contained in the high sweet content *stevia* plant is higher than the average sweet content of all individuals belonging to the segregating population.
[7] The method according to any one of [1] to [6], wherein the sweet component comprises a steviol glycoside.
[8] The method according to any one of [1] to [7], wherein the high sweet content *stevia* plant is a non-genetically modified plant.
[9] The method according to any one of [1] to [8], wherein the test *stevia* plant includes a *stevia* plant subjected to a mutagenesis treatment and a progeny plant thereof.
[10] A primer set comprising a forward primer comprising a sequence which is positioned at the 3' end and selected from SEQ ID NOs: 47 to 70, and an optional sequence which is added to the 5' end of the sequence and is of any consecutive upstream bases following position 28 of SEQ ID NO: 1, and a reverse primer comprising a sequence complementary to a sequence of any consecutive 20 bases or more which is positioned downstream of position 50 of SEQ ID NO: 1.
[11] A kit comprising a primer set according to [10] and a restriction enzyme, wherein in case the forward primer comprises SEQ ID NO: 47, the restriction enzyme is DdeI; in case the forward primer comprises SEQ ID NO: 48, the restriction enzyme is MaeI or SpeI; in case the forward primer comprises SEQ ID NO: 49, the restriction enzyme is AflII or MseI; in case the forward primer comprises SEQ ID NO: 50, the restriction enzyme is Bce83I; in case the forward primer comprises SEQ ID NO: 51, the restriction enzyme is BseMII; in case the forward primer comprises SEQ ID NO: 52, the restriction enzyme is BsiI; in case the forward primer comprises SEQ ID NO: 53, the restriction enzyme is BspHI or Hpy178III; in case the forward primer comprises SEQ ID NO: 54, the restriction enzyme is SfeI; in case the forward primer comprises SEQ ID NO: 55, the restriction enzyme is SmlI; in case the forward primer comprises SEQ ID NO: 56, the restriction enzyme is EcoP15I; in case the forward primer comprises SEQ ID NO: 57, the restriction enzyme is AvaI; in case the forward primer comprises SEQ ID NO: 58, the restriction enzyme is BclI; in case the forward primer comprises SEQ ID NO: 59, the restriction enzyme is BseRI; in case the forward primer comprises SEQ ID NO: 60, the restriction enzyme is CviRI or PstI; in case the forward primer comprises SEQ ID NO:

61, the restriction enzyme is DrdII; in case the forward primer comprises SEQ ID NO: 62, the restriction enzyme is Eco57I; in case the forward primer comprises SEQ ID NO: 63, the restriction enzyme is GsuI; in case the forward primer comprises SEQ ID NO: 64, the restriction enzyme is HphI; in case the forward primer comprises SEQ ID NO: 65, the restriction enzyme is Hpy188I; in case the forward primer comprises SEQ ID NO: 66, the restriction enzyme is MboII; in case the forward primer comprises SEQ ID NO: 67, the restriction enzyme is Pfl1108I; in case the forward primer comprises SEQ ID NO: 68, the restriction enzyme is PsiI; in case the forward primer comprises SEQ ID NO: 69, the restriction enzyme is TaqI or XhoI; and in case the forward primer comprises SEQ ID NO: 70, the restriction enzyme is StySKI.

[12] A high sweet content *stevia* plant having a variation at a portion of the genome corresponding to SEQ ID NO: 1.

[13] The plant according to [12], wherein the variation comprises a variation from C to A at a position corresponding to position 49 of SEQ ID NO: 1.

[14] The plant according to [12] or [13], wherein the plant is a non-genetically modified plant.

[15] A seed, a tissue, a dried leaf, a tissue culture or a cell of the plant according to any one of [12] to [14].

[16] The tissue, tissue culture or the cell according to [15] selected from an embryo, a meristem cell, a pollen, a leaf, a root, a root apex, a petal, a protoplast, a leaf section or a callus.

[17] A method of producing a high sweet content *stevia* plant, the method comprising a step of crossing a *stevia* plant according to any one of [12] to [14] with a second *stevia* plant.

[18] The method according to [17], wherein the second plant is the *stevia* plant according to any one of [12] to [14].

[19] A method of producing a high sweet content *stevia* plant, comprising a step of introducing a variation from C to A to a position corresponding to position 49 of SEQ ID NO: 1 in the genome of a *stevia* plant.

[20] The method according to [19], wherein the introduction of the variation is performed by a mutagenesis treatment.

[21] A method of producing a food or beverage, a sweetener composition, a flavor or a medicament, comprising:

a step of providing an extract of a plant according to any one of [12] to [14], a seed, a tissue, a dried leaf, a tissue culture or a cell according to [15], or a tissue, a tissue culture or a cell according to [16]; and a step of adding the extract to a raw material for the food or beverage, the sweetener composition, the flavor or the medicament.

Advantageous Effects of Invention

The present invention exerts one or more of the following effects.
(1) A *stevia* plant with high content of a sweet component can be selected at low cost.
(2) The time required for the development of the *stevia* plant with high content of a sweet component can be shortened.
(3) The success rate of the development of the *stevia* plant with high content of a sweet component can be increased.
(4) The production efficiency of a sweet component derived from a *stevia* plant can be enhanced.
(5) The cost of production of the sweet component derived from a *stevia* plant can be reduced.

BRIEF DESCRIPTION OF DRAWINGS

FIG. 1 is a diagram showing the frequency distribution of sweet contents in M1 generation individuals. The ordinate depicts the number of individuals, and the abscissa depicts a sweet component concentration (%) in a dried leaf.

FIG. 2 is a diagram showing the distribution of sweet contents in variation C49A positive individuals (C49A$^+$) and negative individuals (C49A$^-$) of segregating population A. The ordinate depicts a sweet component concentration (%) in a dried leaf, and the dotted line depicts the average sweet component concentration of all individuals belonging to the segregating population A.

FIG. 3 is a diagram showing the distribution of sweet contents in variation C49A positive individuals (C49A$^+$) and negative individuals (C49A$^-$) of segregating population B. The ordinate depicts a sweet component concentration (%) in a dried leaf, and the dotted line depicts the average sweet component concentration of all individuals belonging to the segregating population B.

DESCRIPTION OF EMBODIMENTS

Hereinafter, the present invention will be described in detail. The embodiments are given below merely for illustrating the present invention and are not intended to limit the present invention by such embodiments. The present invention can be carried out in various modes without departing from the spirit of the present invention.

Note that all documents, as well as laid-open application publications, patent application publications, and other patent documents cited herein shall be incorporated herein by reference. The present specification incorporates the contents of the specification and the drawings of Japanese Patent Application No. 2018-144512, filed on Jul. 31, 2018, from which the present application claims priority.

1. High Sweet Content *Stevia* Plant

In one aspect, the present invention provides a high sweet content *stevia* plant having a variation at a portion of the genome corresponding to SEQ ID NO: 1 (hereinafter, also referred to as the "plant of the present invention"). The nucleotide sequence represented by SEQ ID NO: 1 is as follows.

TABLE 1

| Nucleotide sequence represented by SEQ ID NO: 1 |
|---|
| SEQ ID NO: 1 | TTATTTAATGATCCAATGGAGGGGGTGATTCAGGTAATAAAA GGCATTCGTATGGAATATACCAAAACATTGCGATTCGTTATT AGCATGGATCTTTCAAGTAATAAACTTATCGGAGAAATACCA GTTGAGTTAACTGCCCTTCATGCCTTGGTGAGTCTCAATTTG TCTAATAATCATCTTATTGGACACATTCCGAATAGCATTGGA AACATGAAAGCTTTAAATTCTCTAGATTTCTCGAGAAACGAG TTAAATGGGTTGATCCCTCCAAGCATTGGAGCTTTGAATTTT TTGAGTCATTTAAATTTGTCAAACAACAACTTATCAGGACCA ATTCCAATCGGAAATCAATTGAGAACCCTCA |

The plant of the present invention is a species derived from a *stevia* plant of wild species, but a genetic variation which increases the sweet content has occurred (hereinafter, may be referred to as the "variation of the present invention").

The phrase "having a variation at a portion of the genome corresponding to SEQ ID NO: 1" means having a variation at a portion consisting of the nucleotide sequence of SEQ ID NO: 1 or a portion consisting of substantially the same nucleotide sequence as that of SEQ ID NO: 1 in the genome of a *stevia* plant. Substantially the same nucleotide sequence as that of SEQ ID NO: 1 means, for example, a nucleotide sequence having a sequence identity of 60% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.1% or more, 98.4% or more, 98.7% or more, 99% or more, 99.2% or more, 99.5% or more or 99.8% or more to the nucleotide sequence of SEQ ID NO: 1. In one embodiment, the portion of the genome corresponding to SEQ ID NO: 1 includes a portion of the genome of a *stevia* plant which is amplified with a forward primer which hybridizes to a portion of 15 to 25 base long from the 5' end of SEQ ID NO: 1, and a reverse primer which hybridizes to a complementary sequence of a portion of 15 to 25 base long from the 3' end of SEQ ID NO: 1. In a specific embodiment, the portion of the genome corresponding to SEQ ID NO: 1 includes a portion of the genome of a *stevia* plant which is amplified with a forward primer having a nucleotide sequence selected from SEQ ID NOs: 2 to 8, and a reverse primer having a nucleotide sequence selected from SEQ ID NOs: 9 to 15.

The phrase "having a variation at a portion of the genome" means differing in one or more bases from the major nucleotide sequence (e.g., SEQ ID NO: 1) of a predetermined portion of the genome of a *stevia* plant. The variation includes a deletion, a substitution and/or an addition of a nucleotide. Furthermore, the variation may be positioned in a coding region or a noncoding region of a gene. In the case of being positioned in a coding region, the variation may or may not involve an amino acid variation.

In one embodiment, the variation includes a variation at the position corresponding to position 11 of SEQ ID NO: 16, the position corresponding to position 21 of SEQ ID NO: 17, the position corresponding to position 31 of SEQ ID NO: 18, the position corresponding to position 41 of SEQ ID NO: 19, or the position corresponding to position 49 of SEQ ID NO: 1 in the genome of a *stevia* plant. The genome of a *stevia* plant may have a portion consisting of a nucleotide sequence identical to SEQ ID NO: 16, 17, 18, 19 or 1, or may have a portion consisting of a nucleotide sequence corresponding to SEQ ID NO: 16, 17, 18, 19 or 1. In the former case, the variation is present at the nucleotide at position 11, 21, 31, 41, or 49 from the 5' end of the portion consisting of a nucleotide sequence identical to SEQ ID NO: 16, 17, 18, 19 or 1 in the genome of a *stevia* plant. On the other hand, in the latter case, since the genome of a *stevia* plant lacks the portion consisting of a nucleotide sequence identical to SEQ ID NO: 16, 17, 18, 19 or 1, the variation is not always present at position 11, 21, 31, 41, or 49 from the 5' end of the portion corresponding to SEQ ID NO: 16, 17, 18, 19 or 1. However, the position corresponding to position 11, 21, 31, 41, or 49 of SEQ ID NO: 16, 17, 18, 19 or 1 in the genome of a *stevia* plant can be identified in consideration of nucleotide sequences upstream and downstream of position 11, 21, 31, 41, or 49 of SEQ ID NO: 16, 17, 18, 19 or 1, etc. For example, the position corresponding to position 11, 21, 31, 41, or 49 of SEQ ID NO: 16, 17, 18, 19 or 1 in the genome of a *stevia* plant can be identified by an alignment analysis of the nucleotide sequence of a portion corresponding to SEQ ID NO: 16, 17, 18, 19 or 1 in the genome of a *stevia* plant with the nucleotide sequence of SEQ ID NO: 16, 17, 18, 19 or 1.

In a specific embodiment, the variation is a substitution of the nucleotide at the position corresponding to position 11 of SEQ ID NO: 16, the position corresponding to position 21 of SEQ ID NO: 17, the position corresponding to position 31 of SEQ ID NO: 18, the position corresponding to position 41 of SEQ ID NO: 19, or the position corresponding to position 49 of SEQ ID NO: 1 in the genome of a *stevia* plant. In a more specific embodiment, the variation is a substitution of C (cytosine) with A (adenine) at the position corresponding to position 11 of SEQ ID NO: 16, the position corresponding to position 21 of SEQ ID NO: 17, the position corresponding to position 31 of SEQ ID NO: 18, the position corresponding to position 41 of SEQ ID NO: 19, or the position corresponding to position 49 of SEQ ID NO: 1 (hereinafter, this variation is also referred to as "C49A") in the genome of a *stevia* plant. A sequence with C substituted with A at position 49 of SEQ ID NO: 1 is shown in SEQ ID NO: 20.

The plant of the present invention is a high sweet content *stevia* plant. The high sweet content *stevia* plant means that the plant has higher content of a sweet component than that of a *stevia* plant lacking the variation of the present invention. The high content of a sweet component means that, for example, in a segregating population obtained by crossing two *stevia* plant individuals, at least any one of which heterozygously has the variation of the present invention, the average or median sweet content of a population of the plants of the present invention (i.e., *stevia* plants having the variation of the present invention) is higher than that of a population of *stevia* plants lacking the variation of the present invention, and/or the plant of the present invention has a sweet content equal to or higher than the average sweet content of all individuals of the segregating population. In one embodiment, the average sweet content of the population of the plants of the present invention belonging to the segregating population is higher by approximately 25% or more, approximately 50% or more, approximately 70% or more, approximately 80% or more, approximately 90% or more, approximately 100% or more, approximately 110% or more, approximately 120% or more, approximately 125% or more, approximately 130% or more, approximately 140% or more, approximately 150% or more, approximately 160% or more, approximately 170% or more, approximately 180% or more, approximately 190% or more or approximately 195% or more than that of a population of *stevia* plants lacking the variation of the present invention which belong to the same segregating population thereas. Furthermore, in one embodiment, the median sweet content of the population of the plants of the present invention belonging to the segregating population is higher by approximately 25% or more, approximately 50% or more, approximately 75% or more, approximately 100% or more, approximately 125% or more, approximately 150% or more, approximately 160% or more, approximately 170% or more, approximately 180% or more, approximately 190% or more, approximately 195% or more, approximately 200% or more or approximately 210% or more than that of a population of *stevia* plants lacking the variation of the present invention which belong to the same segregating population thereas.

The sweet component is not limited as long as the sweet component is contained in a *stevia* plant. Examples of the sweet component include one or more steviol glycosides and combinations thereof. Examples of the steviol glycoside include rebaudioside A, rebaudioside B, rebaudioside C, rebaudioside D, rebaudioside E, rebaudioside F, rebaudioside I, rebaudioside J, rebaudioside K, rebaudioside N, rebaudioside M, rebaudioside O, rebaudioside Q, rebaudioside R, dulcoside A, rubusoside, steviol, steviolmonoside, steviolbioside and stevioside. In one embodiment, the sweet component consists of one or more components selected from rebaudioside A, rebaudioside B, rebaudioside C, rebaudioside D, rebaudioside E, rebaudioside F, rebaudioside I, rebaudioside J, rebaudioside K, rebaudioside N, rebaudioside M, rebaudioside O, rebaudioside Q, rebaudioside R, dulcoside A, rubusoside, steviol, steviolmonoside, steviolbioside and stevioside. In a specific embodiment, the sweet component comprises rebaudioside A, rebaudioside B, rebaudioside C, rebaudioside D, rebaudioside F, rebaudioside N, rebaudioside M and rebaudioside O, or consists of these steviol glycosides.

The *stevia* plant of the present invention is a species derived from a *stevia* plant of wild species, and the aforementioned genetic variation which increases the sweet content has occurred. The genetic variation may occur by a genetic modification approach, or may occur by a non-genetic modification approach. Also, the *stevia* plant of the present invention may have the genetic variation heterozygously or homozygously.

The genetic variation can be detected by PCR method, TaqMan PCR method, sequencing method, microarray method, Invader method, TILLING method, RAD (random amplified polymorphic DNA) method, restriction fragment length polymorphism (RFLP) method, PCR-SSCP method, AFLP (amplified fragment length polymorphism) method, SSLP (simple sequence length polymorphism) method, CAPS (cleaved amplified polymorphic sequence) method, dCAPS (derived cleaved amplified polymorphic sequence) method, allele-specific oligonucleotide (ASO) method, ARMS method, denaturing gradient gel electrophoresis (DGGE) method, CCM (chemical cleavage of mismatch) method, DOL method, MALDI-TOF/MS method, TDI method, padlock probe method, molecular beacon method, DASH (dynamic allele specific hybridization) method, UCAN method, ECA method, PINPOINT method, PROBE (primer oligo base extension) method, VSET (very short extension) method, Survivor assay, Sniper assay, Luminex assay, GOOD method, LCx method, SNaPshot method, Mass ARRAY method, pyrosequencing method, SNP-IT method, melting curve analysis method, etc., but detection methods are not limited thereto. The detailed method of detecting the genetic variation will be mentioned later.

Examples of the "non-genetic modification approach" described herein include a method of inducing a variation in the gene of a host cell (or a host plant) without transfection with a foreign gene. Examples of such a method include a method of allowing a mutagen to act on a plant cell. Examples of such a mutagen include ethyl methanesulfonate (EMS) and sodium azide. For example, EMS can be used at a concentration such as 0.1%, 0.2%, 0.3%, 0.4%, 0.5%, 0.6%, 0.7%, 0.8%, 0.9%, or 1.0% to treat a plant cell. The treatment time is approximately 1 hour to approximately 48 hours, approximately 2 hours to approximately 36 hours, approximately 3 hours to approximately 30 hours, approximately 4 hours to approximately 28 hours, approximately 5 hours to approximately 26 hours, or approximately 6 hours to approximately 24 hours. The procedures themselves of the treatment are known in the art and can be performed by dipping a water-absorbed seed obtained through a water absorption process in a treatment solution containing the mutagen at the concentration described above for the treatment time described above.

Alternative examples of the non-genetic modification approach include a method of irradiating a plant cell with radiation or light beam such as X ray, γ ray, or ultraviolet ray. In the case of performing irradiation with radiation, a cell irradiated using an appropriate dose (ultraviolet lamp intensity, distance, and time) of ultraviolet ray is cultured in a selective medium or the like, and then, a cell, a callus, or a plant having the trait of interest can be selected. In this operation, the irradiation intensity may be 0.01 to 100 Gr, 0.03 to 75 Gr, 0.05 to 50 Gr, 0.07 to 25 Gr, 0.09 to 20 Gr, 0.1 to 15 Gr, 0.1 to 10 Gr, 0.5 to 10 Gr, or 1 to 10 Gr. The irradiation distance may be 1 cm to 200 m, 5 cm to 100 m, 7 cm to 75 m, 9 cm to 50 m, 10 cm to 30 m, 10 cm to 20 m, or 10 cm to 10 m. The irradiation time may be 1 minute to 2 years, 2 minutes to 1 year, 3 minutes to 0.5 years, 4 minutes to 1 month, 5 minutes to 2 weeks, or 10 minutes to 1 week. The irradiation intensity, distance and time differ depending on the type of radiation or light beam or the state of the subject to be irradiated (cell, callus, or plant) and can be appropriately adjusted by those skilled in the art.

Approaches such as cell fusion, another culture (haploid induction), and remote crossing (haploid induction) are also known in the art.

In general, plant cells may involve a mutation during culture. Therefore, it is preferred to regenerate a plant individual, for more stably maintaining the trait.

The scope of the present invention does not exclude a plant obtained by the ex-post facto genetic recombination with a non-genetically modified *stevia* plant as a host (e.g., a plant further provided with another trait by genetic recombination with the plant of the present invention as a host).

The sweet component can be extracted in the state of a liquid extract by reacting a fresh leaf or a dried leaf of the plant of the present invention with a suitable solvent (an aqueous solvent such as water or an organic solvent such as an alcohol, ether or acetone). For the extraction conditions, etc., see a method described in JP 2012-504552 A, or a method described in Examples mentioned later. The dried leaf refers to a leaf having a water content decreased to 10% by weight or less, 7% by weight or less, 5% by weight or less, 4% by weight or less, 3% by weight or less, 2% by weight or less or 1% by weight or less by drying a fresh leaf. Preferably, the water content of the dried leaf of the plant of the present invention is 3 to 4% by weight.

The sweet component can be further purified from the liquid extract thus obtained by use of a method known in the art such as a gradient of ethyl acetate or any of other organic solvents:water, high performance liquid chromatography (HPLC), gas chromatography, time-of-flight mass spectrometry (TOF-MS), or ultra (high) performance liquid chromatography (UPLC).

The sweet content according to the present invention can be measured by a method described in JP 2012-504552 A, or a method described in Examples mentioned later. Specifically, for example, a fresh leaf can be sampled from the *stevia* plant of the present invention, followed by measurement by LC/MS-MS.

The plant of the present invention may include not only the whole plant but a plant organ (e.g., a leaf, a petal, a stem, a root, and a seed), a plant tissue (e.g., epidermis, phloem, soft tissue, xylem, vascular bundle, palisade tissue, and spongy tissue), various forms of plant cells (e.g., suspended cultured cells), a protoplast, a leaf section, a callus, and the like.

The plant of the present invention may also include a tissue culture or a cultured plant cell. This is because the plant can be regenerated by culturing such a tissue culture or a cultured plant cell. Examples of the tissue culture or the cultured plant cell of the plant of the present invention include, but are not limited to, embryos, meristem cells, pollens, leaves, roots, root apices, petals, protoplasts, leaf sections and calluses.

The plant of the present invention may also have, in addition to the variation of the present invention, another variation, for example, a variation positive for at least one dCAPS marker selected from the group consisting of WRKY-02-XbaI, WRKY-08-KpnI, WRKY-09-AflII, WRKY-14 and WD40-01-PvuI. A plant positive for any of these markers has higher content of RebM than that of a negative plant (hereinafter, this variation is also referred to as a "high RebM content variation").

The positivity for WRKY-02-XbaI means that only a band of approximately 383 bp long (approximately 383 bp long; e.g., SEQ ID NO: 23 or 24) is obtained by: performing PCR amplification using a forward primer having the nucleotide sequence shown in SEQ ID NO: 21 and a reverse primer shown in SEQ ID NO: 22 on the genomic DNA of a candidate plant; and treating the obtained PCR product (approximately 383 bp long: e.g., SEQ ID NO: 23 or 24) with an XbaI restriction enzyme. On the other hand, when a restriction enzyme-treated product of approximately 344 bp (e.g., SEQ ID NO: 25) is formed by the XbaI restriction enzyme treatment of the PCR product, the candidate plant is negative for WRKY-02-XbaI.

The positivity for WRKY-08-KpnI means that only a band of approximately 297 bp long (e.g., SEQ ID NO: 28 or 29) is obtained by: performing PCR amplification using a forward primer having the nucleotide sequence shown in SEQ ID NO: 26 and a reverse primer shown in SEQ ID NO: 27 on the genomic DNA of a candidate plant; and treating the obtained PCR product (297 bp long) (e.g., SEQ ID NO: 28 or 29) with a KpnI restriction enzyme. On the other hand, when a restriction enzyme-treated product of approximately 258 bp (e.g., SEQ ID NO: 30) is formed, the candidate plant is negative for WRKY-08-KpnI.

The positivity for WRKY-09-AflII means that only a band of approximately 390 bp long (e.g., SEQ ID NO: 33 or 34) is obtained by: performing PCR amplification using a forward primer having the nucleotide sequence shown in SEQ ID NO: 31 and a reverse primer shown in SEQ ID NO: 32 on the genomic DNA of a candidate plant; and treating the obtained PCR product (approximately 390 bp long) (e.g., SEQ ID NO: 33 or 34) with an AflII restriction enzyme. On the other hand, when a restriction enzyme-treated product of approximately 347 bp (e.g., SEQ ID NO: 35) is formed, the candidate plant is negative for WRKY-09-AflII.

The positivity for WRKY-14 means that only a PCR product of approximately 140 bp (e.g., SEQ ID NO: 38) is formed by performing PCR amplification using a forward primer having the nucleotide sequence shown in SEQ ID NO: 36 and a reverse primer shown in SEQ ID NO: 37 on the genomic DNA of a candidate plant. When PCR products of 140 bp (e.g., SEQ ID NO: 38) and 158 bp (e.g., SEQ ID NO: 39) are formed, the candidate plant is negative therefor.

The positivity for WD40-01-PvuI means that only a band of approximately 288 bp long (e.g., SEQ ID NO: 42 or 43) is obtained by: performing PCR amplification using a forward primer having the nucleotide sequence shown in SEQ ID NO: 40 and a reverse primer shown in SEQ ID NO: 41 on the genomic DNA of a candidate plant; and treating the obtained PCR product (approximately 288 bp long) (e.g., SEQ ID NO: 42 or 43) with a PvuI restriction enzyme. On the other hand, when a restriction enzyme-treated product of approximately 240 bp (e.g., SEQ ID NO: 44) is formed, the candidate plant is negative for WD40-01-PvuI.

The term "approximately" as to bp long described above means±5 bp. The restriction enzyme treatment can be performed according to conditions recommended by the distributor of each restriction enzyme used.

The plant of the present invention may also have, in addition to the aforementioned variation and/or dCAPS marker positive genetic feature, a variation shown in SEQ ID NO: 45, i.e., a variation from wild type A to T at the 60th nucleotide sequence of the corresponding wild type allele nucleotide sequence (SEQ ID NO: 46) (Patent Literature 4).

A plant having this variation has higher content of RebC than that of a plant lacking the variation (hereinafter, this variation is also referred to as a "high RebC content variation").

Since a plant having the variation of the present invention tends to have an elevated content of total sweet component, the combination of the variation of the present invention with other variations mentioned above (e.g., the high RebM content variation and/or the high RebC content variation) can potentiate the effects of these other variations.

2. Method of Producing Plant of Present Invention

In an alternative aspect, the present invention provides a method of producing a *stevia* plant with high content of a sweet component, the method comprising a step of crossing the *stevia* plant of the present invention with a second *stevia* plant (hereinafter, referred to as the "production method of the present invention").

The "a *stevia* plant with high content of a sweet component" produced by the method has the same phenotype and genetic properties as those of the plant of the present invention.

Specifically, the phenotype of the plant produced by the production method of the present invention is the high sweet content phenotype described in the section relating to the plant of the present invention. The genetic properties of the plant produced by the production method of the present invention have the variation of the present invention. The plant produced by the production method of the present invention may have the variation heterozygously or homozygously. A method of detecting such a variation is as mentioned above and mentioned later.

In the production method of the present invention, "hybridizing" means that the plant of the present invention is crossed with a second plant to obtain a child plant thereof (plant produced by the production method of the present invention. The hybridizing method is preferably backcross. The "backcross" is an approach of further crossing a child plant generated between the plant of the present invention and the second plant, with the plant of the present invention (i.e., a plant having the genetic variation of the present invention) to produce a homozygously plant having the genetic variation of the present invention. When the second plant for use in the production method of the present invention has the same phenotype and genetic properties as those of the plant of the present invention, the crossing is substantially backcross. The genetic variation of the present invention is inheritable according to the Mendel's law. In association with this, the phenotype correlating with the genetic variation, i.e., the high content of a sweet component phenotype, is also inheritable according to the Mendel's law.

Alternatively, the plant of the present invention can also be produced by selfing. The selfing can be performed by the self-pollination of the stamen pollen of the plant of the present invention with the pistil of the plant of the present invention.

Since the plant produced by the production method of the present invention has the same phenotype and genetic properties as those of the plant of the present invention, the plant produced by the production method of the present invention can be further crossed with a third *stevia* plant to produce a *stevia* plant with high content of a sweet component.

In an alternative embodiment, the plant of the present invention may be produced by regenerating a plant by the culture of the tissue culture or the cultured plant cell mentioned above. The culture conditions are the same as those for culturing a tissue culture or a cultured plant cell of the wild type *stevia* plant and are known in the art (Protocols for In Vitro cultures and secondary metabolite analysis of aromatic and medicinal plants, Method in molecular biology, vo. 1391, pp. 113-123).

In a further alternative embodiment, the plant of the present invention may be produced by introducing a variation from C to A to a position corresponding to position 49 of SEQ ID NO: 1 in the genome of a *stevia* plant. The introduction of the variation may be performed by a genetic modification approach or may be performed by a non-genetic modification approach. The non-genetic modification approach includes the mutagenesis treatment, such as a treatment with a mutagen or a treatment by irradiation with radiation or light beam, described in the section relating to the plant of the present invention.

3. Method of Screening for Plant of Present Invention

The plant of the present invention can be screened for by detecting the variation of the present invention from a tissue of a test plant. In this context, "screening" means that the plant of the present invention is discriminated from the other plants to select the plant of the present invention.

Thus, in an alternative aspect, the present invention provides a method of screening for a high sweet content *stevia* plant, comprising a step of detecting a variation at a portion corresponding to SEQ ID NO: 1 from the genome of a test *stevia* plant (hereinafter, may be referred to as the "screening method of the present invention"). The "variation at a portion corresponding to SEQ ID NO: 1" (the variation of the present invention) and the "high sweet content *stevia* plant" are as described above about the plant of the present invention.

Specific examples of methods of detecting the genetic variation of the present invention include, but not limited to, PCR method, TaqMan PCR method, sequencing method, microarray method, Invader method, TILLING method, RAD method, RFLP method, PCR-SSCP method, AFLP method, SSLP method, CAPS method, dCAPS method, ASO method, ARMS method, DGGE method, CCM method, DOL method, MALDI-TOF/MS method, TDI method, padlock probe method, molecular beacon method, DASH method, UCAN method, ECA method, PINPOINT method, PROBE method, VSET method, Survivor assay, Sniper assay, Luminex assay, GOOD method, LCx method, SNaPshot method, Mass ARRAY method, pyrosequencing method, SNP-IT method, melting curve analysis method, etc.

In the case of PCR method, it is preferable to generate a primer such that the 3' end portion has a sequence complementary to the variation site of the present invention. By using a primer designed in this way, the polymerase extension reaction proceeds because the primer hybridizes completely to the template if the template sample has the variation, whereas if the template does not have the variation of the present invention, the extension reaction does not occur because the nucleotide at the 3' end of the primer mismatches the template. Therefore, PCR amplification is performed using such a primer, and the amplification product is analyzed by agarose gel electrophoresis or the like, and if an amplification product of a predetermined size can be confirmed, the template as the sample has a variation, and if the amplification product is not present, it can be judged that the template does not have a variation.

Alternatively, the genetic variation of the present invention can be detected by designing the primer sequence so that the variation of the present invention and the primer sequence do not overlap and the genetic variation of the present invention can be PCR amplified, and by sequencing the nucleotide sequence of the amplified nucleotide fragment.

For PCR and agarose gel electrophoresis see Sambrook, Fritsch and Maniatis, "Molecular Cloning: A Laboratory Manual" 2nd Edition (1989), Cold Spring Harbor Laboratory Press.

TaqMan PCR method uses fluorescently labeled allele-specific oligos and Taq DNA polymerases (Livak, K. J. Genet). Anal. 14, 143 (1999); Morris T. et al., J. Clin. Microbiol. 34, 2933 (1996)).

The sequencing method is a method of analyzing the presence or absence of a variation by amplifying a region containing the variation by PCR and sequencing the DNA sequence using a Dye Terminator or the like (Sambrook, Fritsch and Maniatis, "Molecular Cloning: A Laboratory Manual" 2nd Edition (1989), Cold Spring Harbor Laboratory Press).

A DNA microarray is one in which one end of a nucleotide probe is immobilized in an array on a support, and includes a DNA chip, a Gene chip, a microchip, a bead array, and the like. By using a probe containing a sequence complementary to the genetic variation of the present invention, the presence or absence of the genetic variation of the present invention can be comprehensively detected. DNA microarray assays such as DNA chips include GeneChip assays (see Affymetrix; U.S. Pat. Nos. 6,045,996; 5,925,525; and 5,858,659). The GeneChip technique utilizes a miniaturized, high density microarray of oligonucleotide probes affixed to a chip.

The invader method combines the hybridization of two reporter probes specific for each allele of a genetic variation such as SNPs and one invader probe to template DNA and the cleavage of DNA by Cleavase enzyme with a special endonuclease activity which cleaves a DNA by recognizing its structure (Livak, K. J. Biomol. Eng. 14, 143-149 (1999); Morris T. et al., J. Clin. Microbiol. 34, 2933 (1996); Lyamichev, V. et al., Science, 260, 778-783 (1993), and the like).

TILLING (Targeting Induced Local Lesions IN Genomes) method is a method in which mutational mismatches in the genomes of a mutagenized mutant population are screened by PCR-amplification and CEL I nuclease-treatment.

In one embodiment, the variation of the present invention can be detected by dCAPS method using the following primer set and a restriction enzyme.

Primer Set:

A primer set comprising a forward primer comprising a sequence which is positioned at the 3' end and selected from SEQ ID NOs: 47 to 70, and an optional sequence which is added to the 5' end of the sequence and is of any consecutive upstream bases following position 28 of SEQ ID NO: 1 (e.g., a consecutive sequence of any length), and a reverse primer comprising a sequence (e.g., SEQ ID NO: 15 or 71) complementary to a sequence of any consecutive 20 bases or more which is positioned downstream of position 50 of SEQ ID NO: 1.

The sequences of the primers can be optimized within a range that satisfies the conditions described above. For the optimization of primer design, see, for example, Sambrook and Russell, "Molecular Cloning: A Laboratory Manual" 3rd Edition (2001), Cold Spring Harbor Laboratory Press. Each of the primers may be 15 to 50 base length, 18 to 48 base length, 20 to 45 base length, 30 to 65 base length, or the like.

Restriction Enzyme:

A restriction enzyme appropriate for each of SEQ ID NOs: 47 to 70 is shown below. In the sequences described below, "R" represents A or G, and "Y" represents C or T.

TABLE 2

Restriction enzyme appropriate for sequence contained in forward primer

| Sequence contained in forward primer | Restriction enzyme |
|---|---|
| TTCAGGTAATAAAAGGCCTT (SEQ ID NO:47) | DdeI |
| TTCAGGTAATAAAAGGCACT (SEQ ID NO:48) | MaeI/SpeI |
| TTCAGGTAATAAAAGGCTTA (SEQ ID NO:49) | AflII/MseI |
| TTCAGGTAATAAAAGGCTTG (SEQ ID NO:50) | Bce83I |
| TTCAGGTAATAAAAGGCCTC (SEQ ID NO:51) | BseMII |
| TTCAGGTAATAAAAGGCACG (SEQ ID NO:52) | BsiI |
| TTCAGGTAATAAAAGTCATG (SEQ ID NO:53) | BspHI/Hpy178III |
| TTCAGGTAATAAAAGGCTRT (SEQ ID NO:54) | SfeI |
| TTCAGGTAATAAAAGGCTTR (SEQ ID NO:55) | SmlI |
| TTCAGGTAATAAAAGGCAGC (SEQ ID NO:56) | EcoP15I |
| TTCAGGTAATAAAAGGCYCG (SEQ ID NO:57) | AvaI |
| TTCAGGTAATAAAAGTGATC (SEQ ID NO:58) | BclI |
| TTCAGGTAATAAAAGGGAGG (SEQ ID NO:59) | BseRI |
| TTCAGGTAATAAAAGGCTGC (SEQ ID NO:60) | CviRI/PstI |
| TTCAGGTAATAAAAGGAACC (SEQ ID NO:61) | DrdII |
| TTCAGGTAATAAAAGGCTGA (SEQ ID NO:62) | Eco57I |
| TTCAGGTAATAAAAGGCTGG (SEQ ID NO:63) | GsuI |
| TTCAGGTAATAAAAGGGGTG (SEQ ID NO:64) | HphI |
| TTCAGGTAATAAAAGGTCTG (SEQ ID NO:65) | Hpy188I |
| TTCAGGTAATAAAAGGGAAG (SEQ ID NO:66) | MboII |
| TTCAGGTAATAAAAGGTCGT (SEQ ID NO:67) | Pfl1108I |
| TTCAGGTAATAAAAGTTATA (SEQ ID NO:68) | PsiI |
| TTCAGGTAATAAAAGGCTCG (SEQ ID NO:69) | TaqI/XhoI |
| TTCAGGCGATAAAAGGCGTT (SEQ ID NO:70) | StySKI |

In a specific embodiment, the variation of the present invention can be detected by dCAPS method using the following primer set and a restriction enzyme.

TABLE 3

Combination of primer set and restriction enzyme

| Sequence of forward primer | Sequence of reverse primer | Restriction enzyme |
|---|---|---|
| SEQ ID NO:72 | SEQ ID NO:15 | DdeI |
| SEQ ID NO:73 | SEQ ID NO:15 | MaeI/SpeI |
| SEQ ID NO:74 | SEQ ID NO:15 | AflII/MseI |
| SEQ ID NO:75 | SEQ ID NO:15 | Bce83I |
| SEQ ID NO:76 | SEQ ID NO:15 | BseMII |
| SEQ ID NO:77 | SEQ ID NO:15 | BsiI |
| SEQ ID NO:78 | SEQ ID NO:15 | BspHI/Hpy178III |
| SEQ ID NO:79 | SEQ ID NO:15 | SfeI |
| SEQ ID NO:80 | SEQ ID NO:15 | SmlI |
| SEQ ID NO:81 | SEQ ID NO:15 | EcoP15I |
| SEQ ID NO:82 | SEQ ID NO:15 | AvaI |
| SEQ ID NO:83 | SEQ ID NO:15 | BclI |
| SEQ ID NO:84 | SEQ ID NO:15 | BseRI |
| SEQ ID NO:85 | SEQ ID NO:15 | CviRI/PstI |
| SEQ ID NO:86 | SEQ ID NO:15 | DrdII |
| SEQ ID NO:87 | SEQ ID NO:15 | Eco57I |
| SEQ ID NO:88 | SEQ ID NO:15 | GsuI |
| SEQ ID NO:89 | SEQ ID NO:15 | HphI |
| SEQ ID NO:90 | SEQ ID NO:15 | Hpy188I |
| SEQ ID NO:91 | SEQ ID NO:15 | MboII |
| SEQ ID NO:92 | SEQ ID NO:15 | Pfl1108I |
| SEQ ID NO:93 | SEQ ID NO:15 | PsiI |
| SEQ ID NO:94 | SEQ ID NO:15 | TaqI/XhoI |
| SEQ ID NO:95 | SEQ ID NO:15 | StySKI |

The screening methods of the present invention may further comprise a step of determining the sweet content of a tissue of the test *stevia* plant tissue for which the variation of the present invention has been detected. The determination of the sweet content is as described in the section relating to the plant of the present invention. In this embodiment, the screening method of the present invention may be applied to daughter plants obtained by selecting individuals with a higher content of sweet component from among the test *stevia* plants in which the variation of the present invention is detected, and crossing the selected individuals with another *stevia* plants. Thus, the screening method of the present invention may comprise one or more of the following steps.

(i) Detecting the variation at a portion corresponding to SEQ ID NO: 1 from the genome of a test *stevia* plant;

(ii) determining the sweet content of the test *stevia* plant tissue in which the variation has been detected;

(iii) selecting an individual with a higher content of sweet component from among the test *stevia* plants in which the variation of the present invention has been detected;

(iv) crossing the selected individual with a higher content of sweet component with another *stevia* plant;

(v) detecting the variation at a portion corresponding to SEQ ID NO: 1 from the genome of daughter plants obtained by crossing, (vi) measuring the sweet content of the tissue of the daughter plants in which the variation has been detected, (vii) selecting individuals having a higher sweet content from among the daughter plants in which the variation has been detected.

Individuals with a high content of sweet component of choice may be, for example, up to 50%, up to 40%, up to 30%, up to 20%, up to 10%, up to 5%, up to 4%, up to 3%, up to 2%, or up to 1% of the test *stevia* plants in which the variation of the present invention has been detected, with respect to the high content of sweet component. Other *stevia* plants to be crossed may or may not contain the variation of the present invention. In the above embodiment, steps (iv) to (vii) can be repeated a plurality of times. In this way, *stevia* plants with a higher content of sweet component can be screened.

In the screening method of the present invention, the test *stevia* plant may be a natural plant or a non-transgenic plant. Non-transgenic plants are as described in the section relating to the plant of the present invention.

In the screening method of the present invention, the test *stevia* plant may include a *stevia* plant subjected to a mutagenesis treatment and a progeny plant thereof. The mutagenesis treatment is as described in the section relating to the plant of the present invention, and includes treatment with a mutagen, treatment with radiation or irradiation with light, and the like.

In one embodiment, at least one of the crossing parents of the test *stevia* plant in the screening method of the present invention heterozygously has the variation of the present invention, and neither of the crossing parents of the test *stevia* plant homozygously has the variation of the present invention. In this embodiment, the test *stevia* plant belongs to a segregating population resulting from the crossing of two *stevia* plant individuals, at least one of which heterozygously has the variation of the present invention. In the development of a better variety, for example, a variety with higher content of a sweet component, a segregating population may be obtained by the crossing of individuals with high content of a sweet component, or the crossing of an individual with high content of a sweet component with an individual that exhibits other phenotypes, etc. and an individual with high content of a sweet component can be selected from the segregating population. The quantitative determination of the sweet content as to all individuals of the segregating population requires a great deal of time, cost and effort. By contrast, the detection of a genetic variation can be performed with less time, cost and labor as compared with the detection of the sweet content. It has been experimentally confirmed that the variation of the present invention is contained in an individual having a sweet content equal to or higher than the average sweet content of a segregating population resulting from the crossing of two *stevia* plant individuals, at least one of which heterozygously has the variation of the present invention (see Examples). The individual having a sweet content equal to or higher than the average sweet content can be selected from the segregating population by detecting the variation of the present invention. This can drastically reduce the number of individuals to be subjected to sweet content determination, and enables lower cost, speeding up, higher efficiency, improved success rate, etc. of the breeding and development of a *stevia* plant with high content of a sweet component.

The present invention provides a probe capable of detecting the presence and/or absence of the variation of the present invention, which may be referred to as the "probe of the present invention" hereinafter. The probe of the present invention may have a structure suitable for various detection methods for the presence and/or absence of the variation of the present invention. For example, the probe of the present invention may comprise a nucleotide sequence complementary to a portion of a genome or a transcript comprising a variation site of the present invention. Non-limiting examples of such probes include those specifically hybridizing to a nucleotide sequence selected from SEQ ID NOs: 1, 16 to 20 and 99 to 102. Of these sequences, SEQ ID NOs: 20 and 99 to 102 are nucleotide sequences comprising the variation of the present invention, and SEQ ID NOs: 1 and 16 to 19 are nucleotide sequences not comprising the variation of the present invention. In a preferred embodiment, a probe capable of detecting the presence of the variation of the present invention has a hybridization condition wherein the probe hybridizes to the nucleotide sequence selected from SEQ ID NOs: 20 and 99 to 102, but does not hybridize to the nucleotide sequence selected from SEQ ID NOs: 1 and 16 to 19. In a preferred embodiment, a probe capable of detecting the absence of the variation of the present invention has a hybridization condition wherein the probe hybridizes to the nucleotide sequence selected from SEQ ID NOs: 1 and 16 to 19, but does not hybridize to the nucleotide sequence selected from SEQ ID NOs: 20 and 99 to 102.

The presence of the variation of the present invention may be detected by detection of a nucleotide sequence comprising the variation of the present invention and/or by non-detection of a nucleotide sequence not comprising the variation of the present invention, and the absence of the variation of the invention by non-detection of a nucleotide sequence comprising the variation of the present invention and/or by detection of a nucleotide sequence not comprising the variation of the present invention.

The probes of the present invention preferably have a label. Non-limiting examples of such label include a fluorescent label, a luminescent label, a radioactive label, a dye, an enzyme, a quencher, a binding moiety with a detectable label, and the like. In a specific embodiment, the probe of the present invention has a nucleotide sequence which specifically hybridizes to the nucleotide sequence selected from SEQ ID NOs: 1, 16 to 20 and 99 to 102 and a label.

The present invention also provides a primer set comprising a combination of the forward primer and the reverse primer described above, and a kit comprising the primer set and a restriction enzyme appropriate therefor. The present invention further provides a kit comprising a primer set capable of amplifying by PCR a region having a nucleotide sequence selected from SEQ ID NOs: 1, 16 to 20 and 99 to 102, and a probe of the present invention. These primer sets and kits can be used to detect the variation of the present invention, used in the screening methods of the present invention, and the like. These primer sets and kits may also comprise an instruction including an explanation on the detection of variation of the present invention and on the screening method of the present invention, e.g., a written instruction, and media, e.g., a flexible disk, a CD, a DVD, a Blu-ray disk, a memory card, a USB memory, etc., having recorded thereon information regarding the method of use.

4. Extract Derived from Plant of Present Invention and Product Comprising the Extract In a further aspect, the present invention provides a method of producing a *stevia* sweet component-containing extract, comprising a step of obtaining an extract from the plant of the present invention, or a seed or a dried leaf of the plant (hereinafter, may be referred to as the "extract production method of the present invention"). The present invention further provides a method of producing a *stevia* sweet component, comprising a step of purifying the *stevia* sweet component from an extract obtained by the extract production method of the present invention (hereinafter, may be referred to as the "*stevia* sweet component production method of the present invention"). The *stevia* sweet component includes various steviol glycosides as mentioned above. Therefore, the *stevia* sweet component production method of the present invention includes methods of producing individual steviol glycosides.

A *stevia* sweet component-containing extract can be obtained by reacting a fresh leaf or a dried leaf of the plant of the present invention with a suitable solvent (an aqueous solvent such as water or an organic solvent such as an alcohol, ether or acetone). For the extraction conditions, etc., see a method described in JP 2012-504552 A, or a method described in Examples mentioned later.

The *stevia* sweet component can be purified from the *stevia* sweet component-containing extract by use of a method known in the art such as a gradient of ethyl acetate or any of other organic solvents:water, high performance liquid chromatography (HPLC), gas chromatography, time-of-flight mass spectrometry (TOF-MS), or ultra (high) performance liquid chromatography (UPLC).

The extract obtained by the extract production method of the present invention (hereinafter, may be referred to as the "extract of the present invention") has higher content of a sweet component as compared with an extract obtained by a similar method from a *stevia* plant lacking the variation of the present invention. In this context, the "high content of a sweet component" is as described in the section relating to the plant of the present invention.

The extract of the present invention and/or a *stevia* sweet component obtained by the *stevia* sweet component production method of the present invention (hereinafter, may be referred to as the "*stevia* sweet component of the present invention") can be mixed with other components to produce a novel medicament, flavor or food or beverage with increased content of the *stevia* sweet component. Accordingly, in an alternative aspect, the present invention provides a method of producing a medicament, a flavor or a food or beverage, comprising a step of mixing the extract of the present invention and/or a *stevia* sweet component with other components. The present invention further provides a novel medicament, flavor or food or beverage with increased content of a *stevia* sweet component, obtained by the production method. In this context, the food or beverage means a drink and a food. Thus, in one embodiment, the present invention provides a novel medicament, flavor, drink or food and also provides a method of producing the medicament, the flavor, the drink or the food.

5. Nucleotide Sequence Relating to Plant of Present Invention

In another aspect, the present invention provide nucleotide sequences relating to the plant of the present invention. Specific embodiments of the nucleotide sequences relating to the plant of the present invention having the variation of the present invention comprise or consist of a nucleotide sequence selected from SEQ ID NOs: 20 and 99 to 102.

EXAMPLES

Hereinafter, the present invention will be described with reference to Experimental Examples, Examples, etc. However, the present invention is not limited by these specific embodiments.

(1) Isolation of Individual with High Sweet Content (M0 Generation)

Approximately 2000 (based on weight) wild type *stevia* seeds (commercial variety; introduced in August 2014) were divided into 3 groups, each of which was genetically modified by a treatment with 0.1%, 0.2% or 0.3% ethyl methanesulfonate (EMS).

The seeds thus treated with EMS and untreated seeds were seeded in a greenhouse within the Suntory research center to obtain EMS-treated generation (M0 generation) seedlings. No difference in the rate of germination was seen among the treatment concentrations.

An appropriate amount of fresh leaves was sampled from the EMS-treated generation (M0 generation) and untreated individuals, and the concentration of a sweet component was quantitatively determined by LC/MS-MS (Shimadzu LCMS8050). Specifically, 0.25 g of fresh leaves was dried by freeze drying, and 0.05 g of homogenized dry matter thereof was added into pure water. Extraction by ultrasonic treatment for 20 minutes, and centrifugation and filtration were performed to obtain 0.33 ml of a liquid extract. The concentrations of RebA, RebB, RebC, RebD, RebF, RebM, RebN and RebO were quantitatively determined by LC/MS-MS analysis on this liquid extract in a LCMS8050 ion mode (Shimadzu LCMS8050), and the total sum thereof was regarded as the concentration of the sweet component. Individuals having a sweet component concentration of approximately 20% were used as parent individuals 1 (P1). Also, individuals which were derived from other populations of *stevia* plants and had a sweet component concentration of 5% in a dried leaf were selected as parent individuals 2 (P2).

(2) Isolation of High Sweet Content Individual (M1 Generation) and Gene Analysis The first treated generation (M1 generation) seeds were produced by the crossing of the parent individuals 1 (P1) with the parent individuals 2 (P2), and seeded in a greenhouse within the Suntory research center to obtain M1 generation seedlings (segregating population of 1603 individuals). An appropriate amount of fresh leaves was sampled from the M1 generation individuals, and the concentration of a sweet component was quantitatively determined by LC/MS-MS (Shimadzu LCMS8050) in the same way as above. The results are shown in FIG. 1.

Genomic DNA was extracted from fresh leaves of 30 individuals with highest content of the sweet component (high sweet content individuals) and 30 individuals with lowest content of the sweet component (low sweet content individuals), and examined for a variation present only in any one of the individual groups. Among variations detected by the genomic analysis, 306 variations which had a sufficient amount of genomic information (sequence coverage: ×5 or more), had no continuation of variations, and were free from a sequence insertion or deletion were each studied for an individual in which the variation was present. As a result, a variation from C to A (C49A) at position 49 of SEQ ID NO: 1 was found to be present in the high sweet content individuals, but be absent in the low sweet content individuals.

(3) Verification of Relationship Between Variation C49A and Sweet Content

*Stevia* plants heterozygously having the variation C49A were crossed with *stevia* plants lacking the variation C49A to obtain two segregating populations (segregating population A (443 individuals) and segregating population B (446 individuals)). The presence or absence of the variation C49A in each individual of both the segregating populations, and a sweet content were examined. The dCAPS method was used in the examination of the presence or absence of the variation C49A. Genomic DNA was extracted from each individual, and PCR was performed using the primers given below. A restriction enzyme (SpeI) was added to the PCR product, and enzymatic reaction was performed at 37° C. After the restriction enzyme treatment, electrophoresis was performed using a microchip type electrophoresis apparatus LabChip GX Touch HT (PerkinElmer). The marker was identified on the basis of a band pattern after the electrophoresis.

Forward primer: 5'-TTATTTAATGATCCAATG-GAGGGGGTGATTCAGGTAATAAAAGGCACT-3' (SEQ ID NO: 71)

Reverse primer: 5'-TGAGGGTTCTCAATTGATTTCC-GATTGG-3' (SEQ ID NO: 15)

When a restriction enzyme-treated product of approximately 321 bp (e.g., SEQ ID NO: 98) was formed by the SpeI restriction enzyme treatment of the obtained PCR product of approximately 367 bp (e.g., SEQ ID NO: 96 or 97), the test subject was regarded as being positive for the variation C49A.

The quantitative determination of the sweet content was performed in the same way as in (1).

The distribution of sweet contents of variation C49A positive individuals and negative individuals of each segregating population is shown in FIGS. 2 and 3. As is evident from these results, the sweet contents of the variation C49A positive individuals were higher than the average sweet content of each whole segregating population.

The average and median sweet contents of the variation C49A positive individuals and negative individuals in each segregating population are summarized below.

TABLE 4

Average and median sweet component concentrations (%) in dried leaves of each segregating population

| | | Average (%) | Median (%) |
| --- | --- | --- | --- |
| Segregating population A | Whole | 12.3 | 10.4 |
| | C49A+ | 17.4 | 17.3 |
| | C49A− | 7.7 | 7.5 |
| Segregating population B | Whole | 5.5 | 3.7 |
| | C49A+ | 9.8 | 10.0 |
| | C49A− | 3.3 | 3.2 |

The invention claimed is:

1. A method of screening a test *stevia* plant for a high steviol glycoside content, comprising detecting a variation from C to A at a position corresponding to position 49 of SEQ ID NO: 1 in the genome of the test *stevia* plant.

2. The method according to claim 1, wherein the detecting the variation is performed by use of dCAPS method or a PCR method.

3. The method according to claim 1, further comprising determining the content of the steviol glycoside in a tissue of the test *stevia* plant for which the variation has been detected.

4. The method according to claim 1, wherein the test *stevia* plant belongs to a segregating population obtained from crossing parents, at least one of which heterozygously has the variation from C to A at a position corresponding to position 49 of SEQ ID NO: 1, and the content of the steviol glycoside contained in the test *stevia* plant is higher than the average steviol glycoside content of all individuals belonging to the segregating population.

5. The method according to claim 1, wherein the test high *stevia* plant is a non-genetically modified plant.

6. The method according to claim 1, wherein the test *stevia* plant was, prior to the detecting step, subjected to a mutagenesis treatment or wherein the test *stevia* plant is a progeny plant of a *stevia* plant that was subjected to a mutagenesis treatment.

7. A *stevia* plant selected for having a variation from C to A at a position corresponding to position 49 of SEQ ID NO: 1 within its genome and a high steviol glycoside content as compared to a *stevia* plant that does not have the variation from C to A at a position corresponding to position 49 of SEQ ID NO: 1 within its genome.

8. The plant according to claim 7, wherein the plant is a non-genetically modified plant.

9. A seed, a tissue, a dried leaf, a tissue culture or a cell of the plant according to claim 7, wherein the seed, tissue, dried leaf, tissue culture or cell has a variation from C to A at a position corresponding to position 49 of SEQ ID NO: 1 within its genome.

10. The tissue, the tissue culture or the cell according to claim 9, which is an embryo, a meristem cell, a pollen, a leaf, a root, a root apex, a petal, a protoplast, a leaf section, or a callus that has a variation from C to A at a position corresponding to position 49 of SEQ ID NO: 1 within its genome.

11. A method of producing a *stevia* plant, comprising crossing the *stevia* plant according to claim 7 with a second *stevia* plant.

12. The method according to claim 11, wherein the second plant is a high steviol glycoside content *stevia* plant having a variation from C to A at a position corresponding to position 49 of SEQ ID NO: 1 in its genome.

13. A method of producing a high steviol glycoside content *stevia* plant, comprising introducing a variation from C to A to a position corresponding to position 49 of SEQ ID NO: 1 in the genome of a *stevia* plant.

14. The method according to claim 13, wherein the introduction of the variation is performed by a mutagenesis treatment.

15. A method of producing a food or beverage, a sweetener composition, a flavor or a medicament, comprising:
   obtaining an extract from the plant according to claim 7; and
   adding the extract to a raw material for the food or beverage, the sweetener composition, the flavor or the medicament.

16. A method of producing a steviol glycoside-containing extract, comprising:
   obtaining an extract from the plant according to claim 7.

17. A method of producing a steviol glycoside, comprising:
   obtaining an extract from the plant according to claim 7; and
   purifying the steviol glycoside from the extract.

* * * * *